US012766247B2

(12) United States Patent
Littringer et al.

(10) Patent No.: US 12,766,247 B2
(45) Date of Patent: Oct. 20, 2026

(54) DELIVERY DEVICE FOR DELIVERING A DRUG

(71) Applicant: RevIVe Medtech GmbH, Kufstein (AT)

(72) Inventors: Eva Littringer, Kufstein (AT); Monique Hundsbichler-Meulkens, Schwendau (AT); Nicholas Adomakoh, Holzkirchen (DE); Christian Teissl, Innsbruck (AT); Christian Perfler, Hatting (AT); Alexander Koll, Innsbruck (AT); Karlheinz Seyfang, Weissach im Tal (DE); Johannes Raneburger, Rudersdorf (AT)

(73) Assignee: RevIVe Medtech GmbH, Kufstein (AT)

(*) Notice: Subject to any disclaimer, the term of this patent is extended or adjusted under 35 U.S.C. 154(b) by 874 days.

(21) Appl. No.: 17/912,559

(22) PCT Filed: Mar. 16, 2021

(86) PCT No.: PCT/EP2021/056743
§ 371 (c)(1),
(2) Date: Sep. 19, 2022

(87) PCT Pub. No.: WO2021/185875
PCT Pub. Date: Sep. 23, 2021

(65) Prior Publication Data

US 2023/0071053 A1 Mar. 9, 2023

(30) Foreign Application Priority Data

Mar. 20, 2020 (EP) .................................... 20164411

(51) Int. Cl.
*A61M 5/142* (2006.01)
*A61M 5/172* (2006.01)
*A61M 5/36* (2006.01)

(52) U.S. Cl.
CPC ........ *A61M 5/14216* (2013.01); *A61M 5/172* (2013.01); *A61M 5/365* (2013.01); *A61M 2202/064* (2013.01)

(58) Field of Classification Search
CPC .............. A61M 5/1407; A61M 5/1409; A61M 5/16827; A61M 5/16809;
(Continued)

(56) References Cited

U.S. PATENT DOCUMENTS 9,770,551 B1 * 9/2017 Faden ................. A61M 5/1452
10,434,267 B2 * 10/2019 Akouka ............ A61M 15/0065
(Continued)

FOREIGN PATENT DOCUMENTS

WO 2014154777 A1 10/2014

OTHER PUBLICATIONS

International Search Report for PCT/EP2021/056743 Mailed on Apr. 7, 2021.

*Primary Examiner* — Michael J Tsai
*Assistant Examiner* — Katerina A. Wittliff
(74) *Attorney, Agent, or Firm* — SLEMAN & LUND LLP

(57) ABSTRACT

A delivery device for delivering a drug including a housing having an outlet and a cartridge compartment to receive a cartridge filled with an active pharmaceutical formulation in solid form, a transporting mechanism to transport a predetermined amount of the formulation to a flushing position, a pumping mechanism connectable to a solvent reservoir and to deliver solvent from the solvent reservoir towards the outlet, a jetting piston to enter the flushing position and to
(Continued)

Figure 1:
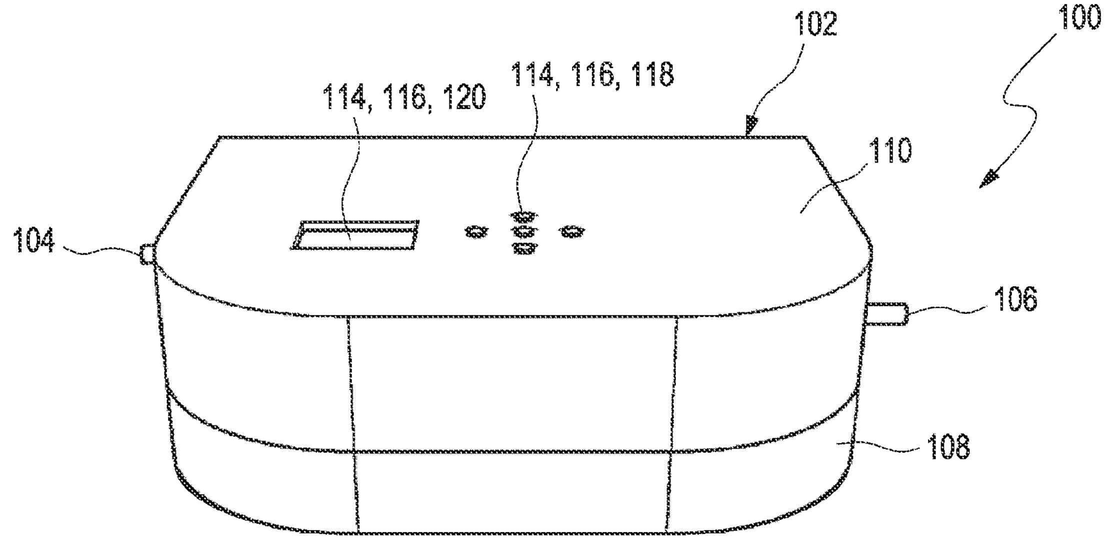

flush the predetermined amount of the formulation from the flushing position with a predetermined amount of the solvent towards the outlet, and a controller to control operation of at least one of the transporting mechanism, the pumping mechanism, the jetting piston.

14 Claims, 10 Drawing Sheets

(58) Field of Classification Search
CPC .. A61M 2005/1402; A61M 2005/1403; A61M 2202/064; A61M 39/24; A61M 5/14216; A61M 5/36; A61M 5/365; A61M 2005/14208; A61M 2205/12; A61M 2205/121; A61M 2205/123; A61M 2205/128; A61M 2205/82; A61M 2205/8206; A61M 15/0028; A61M 15/003; A61M 15/0031; A61M 15/0033; A61M 15/0035; A61M 15/0036; A61M 15/0038; A61M 15/004; A61M 15/0041; A61M 15/0043; A61M 15/0045; A61M 15/0046; A61M 15/0048; A61M 15/005; A61M 15/0051; A61M 15/0053; A61M 15/0055; A61M 15/0056; A61M 15/0058; A61M 15/006; A61M 15/0061; A61M 15/0063
See application file for complete search history.

(56) References Cited

U.S. PATENT DOCUMENTS

| | | | | |
|---|---|---|---|---|
| 2014/0343492 | A1* | 11/2014 | Kamen | A61M 5/16809 604/111 |
| 2016/0378298 | A1* | 12/2016 | Planas | A61M 1/38 715/771 |
| 2019/0111202 | A1* | 4/2019 | Falkovich | A61M 5/14248 |
| 2019/0117879 | A1* | 4/2019 | Imran | A61M 39/0208 |

* cited by examiner

DELIVERY DEVICE FOR DELIVERING A DRUG

FIELD OF THE INVENTION

The present invention relates to a delivery device for continuous or prolonged delivery of a drug, preferably antibiotics in hospital or home setting such as outpatient parenteral antibiotic therapy setting. Particularly, the present invention relates to a mobile, autonomous dosing device for extended or continuous parenteral administration of a drug containing an active pharmaceutical formulation having a reduced decomposition profile allowing superior treatment of antibiotic infections and enabling optimized delivery of antibiotics in terms of pharmacokinetic/pharmacodynamic profile.

BACKGROUND OF THE INVENTION

Several medicines have to be parenterally administered. This applies in particular to medicines, which are deactivated or have their efficiency remarkably decreased by oral administration, e.g. proteins (such as insulin, growth hormones, interferons), carbohydrates (e.g. heparin), antibodies and the majority of vaccines, certain antibiotics. Such medicines are predominantly parenterally administered by means of syringes or delivery devices medicament pumps.

The user of such delivery devices can range from healthcare professionals to the medicament-recipient themselves, the latter ranging from children or elderly persons. The medicinal injections may include repetitive or multiple injections of a particular dose (e.g. a vaccine in multi-dosage regimen) to a single injection of a single dose (e.g. a vaccine or in an emergency hydrocortisone).

As medicament pumps, usually elastomeric, peristaltic or mechanic pumps are used. Despite the advantages provided by delivery devices using such pumps, there are still some drawbacks. All drug delivery devices using conventional medicament pumps have in common that the drug has to be either provided as liquid formulation or needs to be transferred into a liquid formulation (e.g. reconstitution of a lyophilized product in vial) filling into the delivery device and subsequent administration. Thus, there is a risk of contamination. Further, due to limited stability of many drugs in the liquid state compared to the solid state there is the risk of decomposition once in the liquid form and toxic or hazardous degradation products may form in addition to reduced activity due to lower content of the active. Limited stability upon reconstitution is well known for many antibiotics. However, recent studies have shown beneficial effects of prolonged or continuous delivery of parenteral antibiotic solutions, or delivery on demand based on measured blood levels, at intensive care stations as well as in the OPAT (outpatient parenteral antibiotic treatment) setting. However, due to limited stability of many antibiotics in solution, especially at room temperature, it is difficult to provide prolonged or continuous treatment options.

SUMMARY

It is an object of the present disclosure to minimize or eliminate the above drawbacks. Particularly, it is an object to provide a delivery device configured to prepare a predetermined amount of a drug to be administered by solving a predetermined amount of an active pharmaceutical formulation in a solvent within the delivery device as required. Such a drug delivery device is particular used for continuous or prolonged delivery of a drug, preferably antibiotics, in hospital or home setting such as outpatient parenteral antibiotic therapy setting.

As used in the following, the terms “have”, “comprise” or “include” or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions “A has B”, “A comprises B” and “A includes B” may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms “at least one”, “one or more” or similar expressions indicating that a feature or element may be present once or more than once typically will be used only once when introducing the respective feature or element. In the following, in most cases, when referring to the respective feature or element, the expressions “at least one” or “one or more” will not be repeated, non-withstanding the fact that the respective feature or element may be present once or more than once.

Further, as used in the following, the terms “preferably”, “more preferably”, “particularly”, “more particularly”, “specifically”, “more specifically” or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by “in an embodiment of the invention” or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In an aspect of a general concept of the present invention, there is provided a delivery device. The delivery device comprises a housing. The housing comprises an outlet and a cartridge compartment configured to receive a cartridge filled with a sterile active pharmaceutical formulation in solid form, particularly in powder form. The delivery device further comprises a transporting mechanism configured to transport a predetermined amount of the active pharmaceutical formulation to a flushing position. The delivery device further comprises a pumping mechanism connectable to a solvent reservoir and configured to deliver solvent from the solvent reservoir towards the outlet. The delivery device further comprises a jetting piston configured to enter the flushing position and to flush the predetermined amount of the active pharmaceutical formulation from the flushing position with a predetermined amount of the solvent towards the outlet. The delivery device further comprises a controller at least configured to control operation of at least one of the transporting mechanism, the pumping mechanism, the jetting piston.

Thus, the drug may be prepared within the delivery device on demand so as to be fresh and ready to use. Particularly, the transporting mechanism allows to transport a predetermined amount of the active pharmaceutical formulation to a target position when demanded. In one example of the invention, the active pharmaceutical formulation may be provided as compacted powder such as in form of a tablet and the predetermined amount of the active pharmaceutical formulation is separated from the tablet, for example by means of a knife such as a rotating knife. The thus separated predetermined amount of the active pharmaceutical formulation may then be supplied to the flushing position by means of the transporting mechanism. For example, the predetermined amount of the active pharmaceutical formulation may be actively transported or may be supplied to the flushing position by means of a slide or chute. In another example of the invention, the predetermined amount of the active pharmaceutical formulation may already be present in the cartridge. For example, the cartridge may be configured to store one or more pre-prepared doses of the active pharmaceutical formulation such as in the form of loose powder or compacted powder. For example, the cartridge may comprise a plurality of compartments each of which is filled with a predetermined amount of the active pharmaceutical formulation, wherein the compartments are then forwarded to the flushing position in a subsequent order. Thus, any potential degradation the active pharmaceutical formulation in its quality caused by a premature solving of the active pharmaceutical formulation is avoided. The solvent is preferably sucked from the solvent reservoir on demand and does not need to rest for a long time within the delivery device which avoids any potential degradation in its quality. Nevertheless, a temporary storage within the delivery may be acceptable because of the rather small volume within the lines of the delivery 25 device. Further, optionally, a mixing device provides an additional active mixing of the solvent and the predetermined amount of the active pharmaceutical formulation such that a predetermined quality of the mixture and drug, respectively, is ensured. The housing reliably provides protection for the components of the delivery device. The controller allows the operation of the delivery device to be adjusted as appropriate.

The term "delivery device" as used herein is a broad term and is to be given its ordinary and customary meaning to a person of ordinary skill in the art and is not to be limited to a special or customized meaning. The term specifically may refer, without limitation, to any device configured to deliver or administer a drug to a patient. Particularly, the delivery device is configured to deliver or administer a predetermined dose of a drug used for infusion or any other form of administration to a patient such as parenterally.

The term "drug" as used herein is a broad term and is to be given its ordinary and customary meaning to a person of ordinary skill in the art and is not to be limited to a special or customized meaning. The term specifically may refer, without limitation, to a pharmaceutical formulation containing one or more active pharmaceutical ingredients or pharmaceutically acceptable salts or solvates thereof, and optionally pharmaceutically acceptable excipients. An active pharmaceutical ingredient ("API"), in the broadest terms, is a chemical structure that has a biological effect on humans or animals. The term "drug" may be used synonymously to the term "medicament" herein. In pharmacology, a drug or medicament is used in the treatment, cure, prevention, or diagnosis of disease or used to otherwise enhance physical or mental wellbeing. A drug or medicament may be used for a limited duration, or on a regular basis for chronic disorders.

The term "housing" as used herein is a broad term and is to be given its ordinary and customary meaning to a person of ordinary skill in the art and is not to be limited to a special or customized meaning. The term specifically may refer, without limitation, to a shell or material at least partially enclosing or surrounding other or further constructional members.

The term "outlet" as used herein is a broad term and is to be given its ordinary and customary meaning to a person of ordinary skill in the art and is not to be limited to a special or customized meaning. The term specifically may refer, without limitation, to a constructional member allowing the escape or discharge of something. The outlet may be or comprise an opening, orifice, vent or similar passage allowing escape or discharge of the drug.

The term "cartridge" as used herein is a broad term and is to be given its ordinary and customary meaning to a person of ordinary skill in the art and is not to be limited to a special or customized meaning. The term specifically may refer, without limitation, to a pre-formed packaging for pharmaceuticals. Specifically, the cartridge may refer to a "blister pack". The term "blister pack" may refer to a pre-formed plastic packaging used for pharmaceuticals. The primary component of a blister pack is a cavity or pocket made from a formable web, usually a thermoformed plastic. This usually has a backing of paperboard or a lidding seal of aluminum foil or plastic. A blister that folds onto itself is often called a clamshell. Blister packs are useful for protecting products against external factors, such as humidity and contamination for extended periods of time. Opaque blisters also protect light-sensitive products against UV rays.

The term "compartment" as used herein is a broad term and is to be given its ordinary and customary meaning to a person of ordinary skill in the art and is not to be limited to a special or customized meaning. The term specifically may refer, without limitation, to a separate part of a piece equipment, cartridge or a container with a particular purpose. The compartment may be formed by a pocket, cavity indentation or depression in a soft or rigid material which may be closed.

The term "active pharmaceutical formulation" as used herein is a broad term and is to be given its ordinary and customary meaning to a person of ordinary skill in the art and is not to be limited to a special or customized meaning. The term specifically may refer, without limitation, to an ingredient in a pharmaceutical drug that is biologically active. Some drugs or medicines may contain more than one active ingredient or active pharmaceutical formulation. Specifically, the term "active pharmaceutical formulation" may refer to an antimicrobial substance active against bacteria and suitable excipients.

The term "powder" as used herein is a broad term and is to be given its ordinary and customary meaning to a person of ordinary skill in the art and is not to be limited to a special or customized meaning. The term specifically may refer, without limitation, to a conglomeration of discrete solid particles having a particle size D50 of less than 1.0 mm. These fine particles may be the result of reducing dry substance by pounding, grinding, triturating, freeze-drying, spray-drying, crystallization, solvent evaporation etc. It is explicitly stated that the term "powder" may also refer to compacted powder. For example, the compacted powder may be provided as a capsule, tablet or the like.

The term "solvent" as used herein is a broad term and is to be given its ordinary and customary meaning to a person of ordinary skill in the art and is not to be limited to a special or customized meaning. The term specifically may refer, without limitation, to a substance that dissolves a solute, i.e. a chemically distinct liquid, solid or gas, resulting in a solution. A solvent is usually a liquid.

The term "transporting mechanism" as used herein is a broad term and is to be given its ordinary and customary meaning to a person of ordinary skill in the art and is not to be limited to a special or customized meaning. The term specifically may refer, without limitation, to any constructional member that is configured to move or transport the cartridge to a predetermined positions such as the opening position. The transporting mechanism may be a mechanical transporting mechanism, which is manually or electrically driven.

The term "pumping mechanism" as used herein is a broad term and is to be given its ordinary and customary meaning to a person of ordinary skill in the art and is not to be limited to a special or customized meaning. The term specifically may refer, without limitation, to any constructional member that is configured to take or suck the solvent from the reservoir and supply or discharge it to a target such as the outlet. The pumping mechanism may be mechanically or electrically driven.

The term "jetting piston" as used herein is a broad term and is to be given its ordinary and customary meaning to a person of ordinary skill in the art and is not to be limited to a special or customized meaning. The term specifically may refer, without limitation, to a piston that is configured to penetrate into a compartment and to produce a jet of the solvent so as to flush the compartment. The jetting piston may be mechanically or electrically driven.

The cartridge may comprise a plurality of compartments each of which is filled with the predetermined amount of the active pharmaceutical formulation, wherein the transporting mechanism is configured to transport the compartments to the flushing position in a subsequent order. Thus, the predetermined amount of the active pharmaceutical formulation is prepared beforehand and ready to use. With this construction, the compartment at the flushing position may only be opened by means of the jetting piston at the point of time when demanded. Further, a dose of the drug may be controlled by means of the speed of the cartridge. For example, the dose may be controlled by adjusting the supply rate of compartments such as a certain number of compartments per hour. The adjustment controlling of the dose may be realized in a static manner such as by means of pre-setting or in a dynamic manner by means of a feedback loop such as by means of measuring relevant indicators.

The cartridge compartment may be configured to receive a cartridge supply reel on which the cartridge is reeled. Thus, the cartridge may be stored or provided in a rather compact manner which reduces the space necessary for accommodating the cartridge.

The term "reel" as used herein is a broad term and is to be given its ordinary and customary meaning to a person of ordinary skill in the art and is not to be limited to a special or customized meaning. The term specifically may refer, without limitation, to a round, wheel-shaped object on which something, such as the cartridge, can be rolled and stored.

The transporting mechanism may comprise a cartridge drive configured to rotate the cartridge supply reel. The cartridge drive may be an electrical drive. Thus, the cartridge may be exactly moved. The cartridge drive may rotate the cartridge supply reel directly or in an indirect manner.

The delivery device may further comprise a removal reel configured to be reeled with the cartridge after discharging of the active pharmaceutical formulation from at least one of the compartments at the flushing position. Thus, the cartridge may be stored within the delivery device after use in a rather compact manner which reduces infectious hazard.

The cartridge drive may comprise a cartridge drive gear configured to mesh with a removal reel gear, wherein the cartridge supply reel is concertedly rotatable with the removal reel. For example, the cartridge may be connected to the cartridge supply reel and the removal reel such that the cartridge supply reel is rotated by means of the cartridge when the removal reel is driven. Thus, the target position for the cartridge may be exactly defined.

The delivery device may further comprise a removing device configured to remove a foil sealing the compartments arranged at least partially between the cartridge compartment and the flushing position. Alternatively, the jetting piston may be configured to pierce a foil sealing the compartments. Thus, the active pharmaceutical formulation is exposed shortly before it is intended to be flushed with the solvent which avoids any degradation in its quality.

The cartridge may be a sterile blister tape, wherein the compartments may be formed as closed pockets. Such blister tapes are commercially available and common art in the field of the present invention. Thus, the delivery device may use cost effective devices for supplying the active pharmaceutical formulation.

The term "blister tape" as used herein is a broad term and is to be given its ordinary and customary meaning to a person of ordinary skill in the art and is not to be limited to a special or customized meaning. The term specifically may refer, without limitation, to a tape shaped blister pack. A tape is a long, narrow, thin strip of material.

The delivery device may further comprise a fluid channel in fluid communication with the solvent reservoir and the outlet, wherein the jetting piston may be moveable between a retracted position, where the fluid channel is blocked, and an extended position, where the jetting piston provides a fluid communication with the fluid channel and the flushing position. Thus, an exactly defined amount of the solvent and the active pharmaceutical formulation may be supplied towards the outlet.

The term "fluid channel" as used herein is a broad term and is to be given its ordinary and customary meaning to a person of ordinary skill in the art and is not to be limited to a special or customized meaning. The term specifically may refer, without limitation, to a passage through which a fluid such as a liquid, a gas or a mixture thereof may pass or flow.

The pumping mechanism may comprise a pump, e.g. a syringe pump, configured to suck the predetermined amount of the solvent from the solvent reservoir and a non-return valve configured to block a flow of the sucked predetermined amount of the solvent back to the solvent reservoir. Such devices operate in an accurate and reliable manner. The non-return valve prevents solvent from flowing back to the solvent reservoir such that any infectious hazard or inaccuracies in the delivered amounts of the solvent and the active pharmaceutical formulation are avoided.

The term "pump" as used herein is a broad term and is to be given its ordinary and customary meaning to a person of ordinary skill in the art and is not to be limited to a special or customized meaning. The term specifically may refer, without limitation, to a device that moves fluids such as liquids or gases or sometimes slurries, by mechanical action. Pumps can be classified into three major groups according to the method they use to move the fluid: direct lift, displacement, and gravity pumps. Pumps operate by some mechanism (typically reciprocating or rotary), and consume energy to perform mechanical work moving the fluid.

The term "syringe pump" as used herein is a broad term and is to be given its ordinary and customary meaning to a person of ordinary skill in the art and is not to be limited to a special or customized meaning. The term specifically may refer, without limitation, to a small infusion pump (some include infuse and withdraw capability), used to gradually administer small amounts of fluid (with or without medication) to a patient or for use in chemical and biomedical research. An infusion pump infuses fluids, medication or nutrients into a patient's circulatory system. It is generally used intravenously, although subcutaneous, arterial and epidural infusions are occasionally used. Infusion pumps can administer fluids in ways that would be impractically expensive or unreliable if performed manually by nursing staff. For example, they can administer as little as 0.1 mL per hour injections (too small for a drip), injections every minute, injections with repeated boluses requested by the patient, up to maximum number per hour (e.g. in patient-controlled analgesia), or fluids whose volumes vary by the time of day. Because they can also produce quite high but controlled pressures, they can inject controlled amounts of fluids subcutaneously (beneath the skin), or epidurally (just within the surface of the central nervous system). Further, syringe pumps can handle solutions having a rather high viscosity such as with biologics or solutions having a high concentration of the solute.

The term "mixing device" as used herein is a broad term and is to be given its ordinary and customary meaning to a person of ordinary skill in the art and is not to be limited to a special or customized meaning. The term specifically may refer, without limitation, to a device that is configured to provide a mixture. Mixing is a unit operation that involves manipulation of a heterogeneous physical system with the intent to make it more homogeneous. A mixture is a material made up of two or more different substances which are physically combined. A mixture is the physical combination of two or more substances in which the identities are retained and are mixed in the form of solutions, suspension and colloids. Mixtures are one product of mechanically blending or mixing chemical substances such as elements and compounds, without chemical bonding or other chemical change, so that each ingredient substance retains its own chemical properties and makeup. Mixtures can be either homogeneous or heterogeneous. A mixture in which its constituents are distributed uniformly is called homogeneous mixture. A mixture in which its constituents are not distributed uniformly is called heterogeneous mixture. Specifically, the term "mixture" may refer to a combination of two components such as the solvent and the active pharmaceutical formulation representing or forming the drug. The mixing device may also comprise or include a mixing sensor configured to detect the quality of the solution provided by the mixing device such as the degree and/or homogeneity of the thus prepared solution.

The mixing may be realized by micro-fluidic turbulences. For example, the fluid channel may comprise constructional members such as obstacles or deflections causing turbulences within the solvent and the active pharmaceutical formulation.

The mixing device may comprise a mixing chamber configured to receive the predetermined amount of the solvent and the predetermined amount of the active pharmaceutical formulation flushed from the flushing position.

The term "chamber" as used herein is a broad term and is to be given its ordinary and customary meaning to a person of ordinary skill in the art and is not to be limited to a special or customized meaning. The term specifically may refer, without limitation, to a room or spaced used for a special purpose. Specifically, the mixing chamber is a room or space used for mixing purpose.

The mixing device may comprise an ultrasound source configured to emit ultrasound, wherein the ultrasound source is preferably arranged at a position allowing to emit ultrasound into the mixing chamber.

The mixing device may further comprise a stirring member located within the mixing chamber. Thus, an accurate quality of the mixture may be defined.

The term "stirring member" as used herein is a broad term and is to be given its ordinary and customary meaning to a person of ordinary skill in the art and is not to be limited to a special or customized meaning. The term specifically may refer, without limitation, to a member used for stirring purpose. Stirring members are used for mixing of substantially liquid components.

The stirring member may be a magnetic stirring member, wherein the mixing device may further comprise a stirring member drive configured to rotate the stirring member. Thus, the solvent and the active pharmaceutical formulation are reliably mixed in an active manner.

The term "magnetic stirring member" as used herein is a broad term and is to be given its ordinary and customary meaning to a person of ordinary skill in the art and is not to be limited to a special or customized meaning. The term specifically may refer, without limitation, to a magnetic bar placed within a liquid which provides the stirring action. Particularly, the liquid is provided by the mixture of the solvent and the active pharmaceutical formulation. The stir bar's motion is driven by another rotating magnet or assembly of electromagnets in the stirrer device. Stir bars are typically coated in PTFE, or, less often, in glass; the coatings are intended to be chemically inert, not contaminating or reacting with the reaction mixture they are in. Glass coatings are used for liquid alkali metals (except lye, which will eat through glass) and alkali metal solutions in ammonia. They are bar shaped and often octagonal in cross-section (sometimes circular), although a variety of special shapes exist for more efficient stirring. Most stir bars have a pivot ring around the center on which they rotate. The smallest are only a few millimeters long and the largest a few centimeters. A stir bar retriever is a separate magnet on the end of a long stick (usually coated with PTFE) which can be used to remove stir bars from a vessel. Using a magnetic stirring member, the mixing device may be called a magnetic mixer in this case. A magnetic mixer is a device that employs a rotating magnetic field to cause a stir bar (or flea) immersed in a liquid to spin very quickly, thus stirring it. The rotating field may be created either by a rotating magnet or a set of stationary electromagnets, placed beneath the vessel with the liquid. Magnetic stirrers are often used in chemistry and biology, where they can be used inside hermetically closed chamber, vessels or systems, without the need for complicated rotary seals. They are preferred over gear-driven motorized stirrers because they are quieter, more efficient, and have no moving external parts to break or wear out (other than the simple bar magnet itself). Magnetic stir bars work well chambers or containers that do not appreciably affect a magnetic field. Because of its rather small size, a stirring bar is more easily cleaned and sterilized than other stirring devices. They do not require lubricants which could contaminate the reaction room and the product. Magnetic stirrers may also include a hot plate or some other means for heating the liquid.

The stirring member drive may be spatially separated from the mixing chamber. Thus, the risk of any leakage is avoided and a hygienic mixing device is provided.

The controller may be configured to control operation of the mixing device. Thereby, the mixing quality may be controlled.

The delivery device may further comprise a power source, particularly a rechargeable power source, configured to supply electrical power to at least one of the transporting mechanism, the pumping mechanism, the jetting piston, the controller and the mixing device. Thus, all operations may be carried out in an automated manner and any variations in the operation caused by manual handling are avoided. This also makes the device independent from gravity and therefore in any orientation of the patient.

The controller may comprise an interface configured to provide a communication link between the controller and a remote electronic device.

Thus, the operation of the delivery device may be remotely controlled which even allows to provide service support for an user.

The communication link may be realized in a wireless manner. Alternatively, the communication link may be realized in a wired manner. Thus, a remote control of the operation is realized in a flexible way as appropriate. In one embodiment of the invention, the dose may be autonomously optimized via remote control, e.g. by taking into account in situ patient data, and/or by considering expert knowledge, artificial intelligence, big data, and the like.

The delivery device may further comprise an input device configured to allow a user to input instructions to the controller. Thus, even the user may adjust the operation, e.g. if different types of active pharmaceutical formulations are intended to be used.

The input device may comprise a display, a keyboard and/or buttons configured to allow a user to input instructions to the controller. Thus, there are provided different ways to control operation and to input respective instructions.

The delivery device may further comprise a gas separator configured to separate gas, particularly air, from the predetermined amount of the solvent and the predetermined amount of the active pharmaceutical formulation flushed from the flushing position. Thus, any potential degradation of the drug caused by gas bubbles is avoided.

The gas separator may be arranged adjacent the outlet. Thus, the gas may be separated shortly before the drug is delivered from the delivery device. For example, the gas separator may be arranged adjacent or within the mixing device.

The delivery device may further comprise a gas sensor configured to detect gas bubbles, particularly air bubbles, within the predetermined amount of the solvent and the predetermined amount of the active pharmaceutical formulation flushed from the flushing position. Thus, it may be detected whether any particles or bubbles are present in the mixture of the solvent and the active pharmaceutical formulation.

The gas sensor may be further configured to detect a concentration of the predetermined amount of the active pharmaceutical formulation solved within the predetermined amount of the solvent. Thus, it may be detected whether a correct or target concentration of the active pharmaceutical formulation is provided.

The delivery device may further comprise a sterilizing device configured to sterilize the drug. Thus, any infectious hazard of the drug may be avoided.

The term "sterilizing device" as used herein is a broad term and is to be given its ordinary and customary meaning to a person of ordinary skill in the art and is not to be limited to a special or customized meaning. The term specifically may refer, without limitation, to a device used to make something completely clean and free from bacteria.

The sterilizing device may be a UVC light source. Such a device is rather compact which reduces the overall size of the delivery device.

The term "UVC light source" as used herein is a broad term and is to be given its ordinary and customary meaning to a person of ordinary skill in the art and is not to be limited to a special or customized meaning. The term specifically may refer, without limitation, to a source configured to emit light with a wavelength of 100 nm to 280 nm.

The delivery device may further comprise at least one position sensor configured to detect a position of the cartridge. Thus, it may be detected whether the cartridge is at a target position.

The delivery device may be a portable delivery device. Thus, the delivery device may be designed in a rather compact or small manner.

The term "portable" as used herein is a broad term and is to be given its ordinary and customary meaning to a person of ordinary skill in the art and is not to be limited to a special or customized meaning. The term specifically may refer, without limitation, to the dimensions and weight of the delivery device allowing a user such as a human being to lift or carry the device.

The pumping mechanism may comprise an inlet connectable to the solvent reservoir which in turn may be internal or external to the housing.

The term "inlet" as used herein is a broad term and is to be given its ordinary and customary meaning to a person of ordinary skill in the art and is not to be limited to a special or customized meaning. The term specifically may refer, without limitation, to a constructional member allowing the entry or supply of something. The inlet may be or comprise an opening, orifice, vent or similar passage allowing escape or discharge of the solvent.

The delivery device may be configured to communicate with an in-situ blood sensor. Thus, the dose of the drug may be adapted to blood values detected by the blood sensor. Particularly, patients in an intensive care have concentration of antibiotics varying over time as the kidney do not properly operate. The variation may be rapid and involve a significant degradation of the concentration of the antibiotics such that the medicine does not work well or even rises and becomes toxic. Thus, a precise dosing may be provided by the communication with such a blood sensor. Further, a dose of the drug may be controlled by means of the speed of the cartridge. For example, the dose may be controlled by adjusting the supply rate of compartments such as a certain number of compartments per hour. The adjustment controlling of the dose may be realized in a static manner such as by means of pre-setting or in a dynamic manner by means of a feedback loop such as by means of measuring relevant indicators.

The delivery device may be a single use device.

Alternatively, the delivery device may be reusable, wherein the cartridge compartment is configured to allow a replacement of the cartridge.

The delivery device may further comprise a filter upstream the outlet. Thus, any potential particles such as resulting from the penetration of the sealing foil may be reliably be removed from the drug.

Summarizing and without excluding further possible embodiments, the following embodiments may be envisaged:

Embodiment 1: A delivery device for delivering a drug, comprising a housing having an outlet and a cartridge compartment configured to receive a cartridge filled with a sterile active pharmaceutical formulation in solid form, particularly in powder form, a transporting mechanism configured to transport an predetermined amount of the active pharmaceutical formulation to a flushing position, a pumping mechanism connectable to a solvent reservoir and configured to deliver a solvent from the solvent reservoir towards the outlet, and a jetting piston configured to enter the flushing position and to flush the predetermined amount of the active pharmaceutical formulation from the flushing position with a predetermined amount of the solvent towards the outlet, and a controller configured to control operation of at least one of the transporting mechanism, the pumping mechanism, the jetting piston.

Embodiment 2: The delivery device according to the preceding embodiment, wherein the cartridge comprises a plurality of compartments each of which is filled with the predetermined amount of the active pharmaceutical formulation, wherein the transporting mechanism is configured to transport the compartments to the flushing position in a subsequent order.

Embodiment 3: The delivery device according to the preceding embodiment, wherein the cartridge compartment is configured to receive a cartridge supply reel on which the cartridge is reeled.

Embodiment 4: The delivery device according to the preceding embodiment, wherein the transporting mechanism comprises a cartridge drive configured to rotate the cartridge supply reel.

Embodiment 5: The delivery device according to the preceding embodiment, further comprising a removal reel configured to be reeled with the cartridge after discharging of the active pharmaceutical formulation from at least one of the compartments at the flushing position.

Embodiment 6: The delivery device according to the preceding embodiment, wherein the cartridge drive comprises a cartridge drive gear configured to mesh with a removal reel gear of the removal reel, wherein the cartridge supply reel is concertedly rotatable with the removal reel.

Embodiment 7: The delivery device according to any one of embodiments 2 to 6, further comprising a removing device configured to remove a foil sealing the compartments arranged at least partially between the cartridge compartment and the flushing position or the jetting piston is configured to pierce a foil sealing the compartments.

Embodiment 8: The delivery device according to any one of embodiments 2 to 7, wherein the cartridge is a blister tape, wherein the compartments are formed as closed pockets.

Embodiment 9: The delivery device according to any preceding embodiment, further comprising a fluid channel in fluid communication with the solvent reservoir and the outlet, wherein the jetting piston is moveable between a retracted position, where the fluid channel is blocked, and an extended position, where the jetting piston provides a fluid communication with the fluid channel and the flushing position.

Embodiment 10: The delivery device according to any preceding embodiment, wherein the pumping mechanism comprises a pump, particularly a syringe pump, configured to suck the predetermined amount of the solvent from the solvent reservoir and a non-return valve configured to block a flow of the sucked predetermined amount of the solvent back to the solvent reservoir.

Embodiment 11: The delivery device according to any preceding embodiment, further comprising a mixing device being in fluid communication with the outlet and configured to mix the predetermined amount of the solvent and predetermined amount of the active pharmaceutical formulation flushed from the flushing position so as to provide the drug.

Embodiment 12: The delivery device according to the preceding embodiment, wherein the mixing is realized by micro-fluidic turbulences.

Embodiment 13 The delivery device according to embodiment 11 or 12, wherein the mixing device comprises a mixing chamber configured to receive the predetermined amount of the solvent and the predetermined amount of the active pharmaceutical formulation flushed from the flushing position.

Embodiment 14: The delivery device according to the preceding embodiment, wherein the mixing device comprises an ultrasound source configured to emit ultrasound, wherein the ultrasound source is preferably arranged at a position allowing to emit ultrasound into the mixing chamber.

Embodiment 15: The delivery device according to embodiment 13, wherein the mixing device further comprises a stirring member located within the mixing chamber.

Embodiment 16: The device according to the preceding embodiment, wherein the stirring member is a magnetic stirring member, wherein the mixing device further comprises a stirring member drive configured to rotate the stirring member.

Embodiment 17: The delivery device according to the preceding embodiment, wherein the stirring member drive is spatially separated from the mixing chamber.

Embodiment 18: The delivery device according to any one of embodiments 11 to 17, wherein the controller is configured to control operation of the mixing device.

Embodiment 19: The delivery device according to any preceding embodiment, further comprising a power source, particularly a rechargeable power source, configured to supply electrical power to at least one of the transporting mechanism, the pumping mechanism, the jetting piston, the controller and the mixing device.

Embodiment 20: The delivery device according to any preceding embodiment, wherein the controller comprises an interface configured to provide a communication link between the controller and a remote electronic device.

Embodiment 21: The delivery device according to the preceding embodiment, wherein the communication link is realized in a wireless or wired manner.

Embodiment 22: The delivery device according to any preceding embodiment, further comprising an input device configured to allow a user to input instructions to the controller.

Embodiment 23: The delivery device according to the preceding embodiment, wherein the input device comprises a display, a keyboard and/or buttons configured to allow a user to input instructions to the controller.

Embodiment 24: The delivery device according to any preceding embodiment, further comprising a gas separator configured to separate gas, particularly air, from the predetermined amount of the solvent and the predetermined amount of the active pharmaceutical formulation flushed from the flushing position.

Embodiment 25: The delivery device according to the preceding embodiment, wherein the gas separator is arranged adjacent the outlet.

Embodiment 26: The delivery device according to any preceding embodiment, further comprising a gas sensor configured to detect gas bubbles, particularly air bubbles, within the predetermined amount of the solvent and the predetermined amount of the active pharmaceutical formulation flushed from the flushing position.

Embodiment 27: The delivery device according to the preceding embodiment, wherein the gas sensor is further configured to detect a concentration of the predetermined amount of the active pharmaceutical formulation solved within the predetermined amount of the solvent.

Embodiment 28: The delivery device according to any preceding embodiment, further comprising a sterilizing device configured to sterilize the drug.

Embodiment 29: The delivery device according to the preceding embodiment, wherein the sterilizing device is a UVC light source.

Embodiment 30: The delivery device according to any preceding embodiment, further comprising at least one position sensor configured to detect a position of the cartridge.

Embodiment 31: The delivery device according to any preceding embodiment, wherein the delivery device is a portable delivery device.

Embodiment 32: The delivery device according to any preceding embodiment, wherein the pumping mechanism comprises an inlet connectable to the solvent reservoir internal or external to the housing.

Embodiment 33: The delivery device according to any preceding embodiment, wherein the delivery device is configured to communicate with an in-situ blood sensor.

Embodiment 34: The delivery device according to any preceding embodiment, wherein the delivery device is a single use device.

Embodiment 35: The delivery device according to any one of embodiments 1 to 33, wherein the delivery device is reusable, wherein the cartridge compartment is configured to allow a replacement of the cartridge.

Embodiment 36: The delivery device according to any preceding embodiment, further comprising a filter upstream the outlet.

SHORT DESCRIPTION OF THE FIGURES

Further optional features and embodiments will be disclosed in more detail in the subsequent description of embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 2:
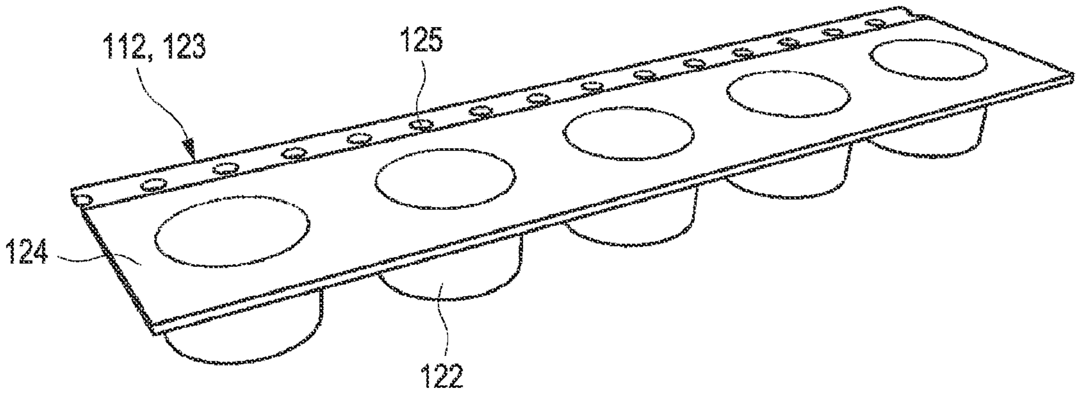
Figure 3:
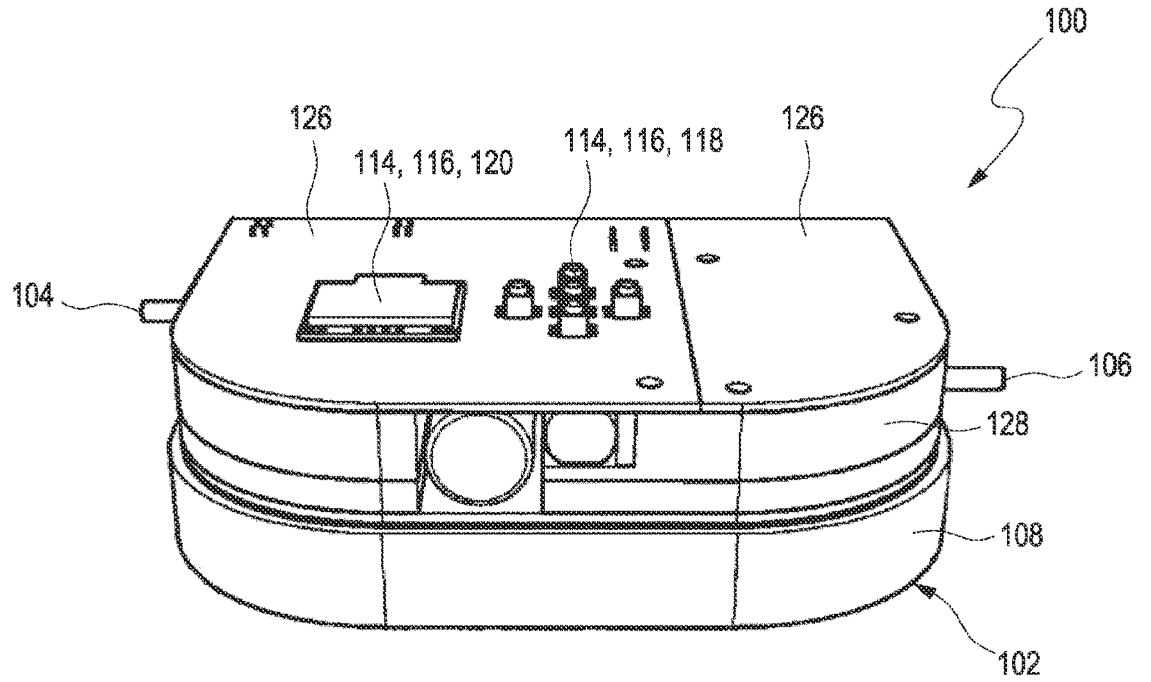
Figure 4:
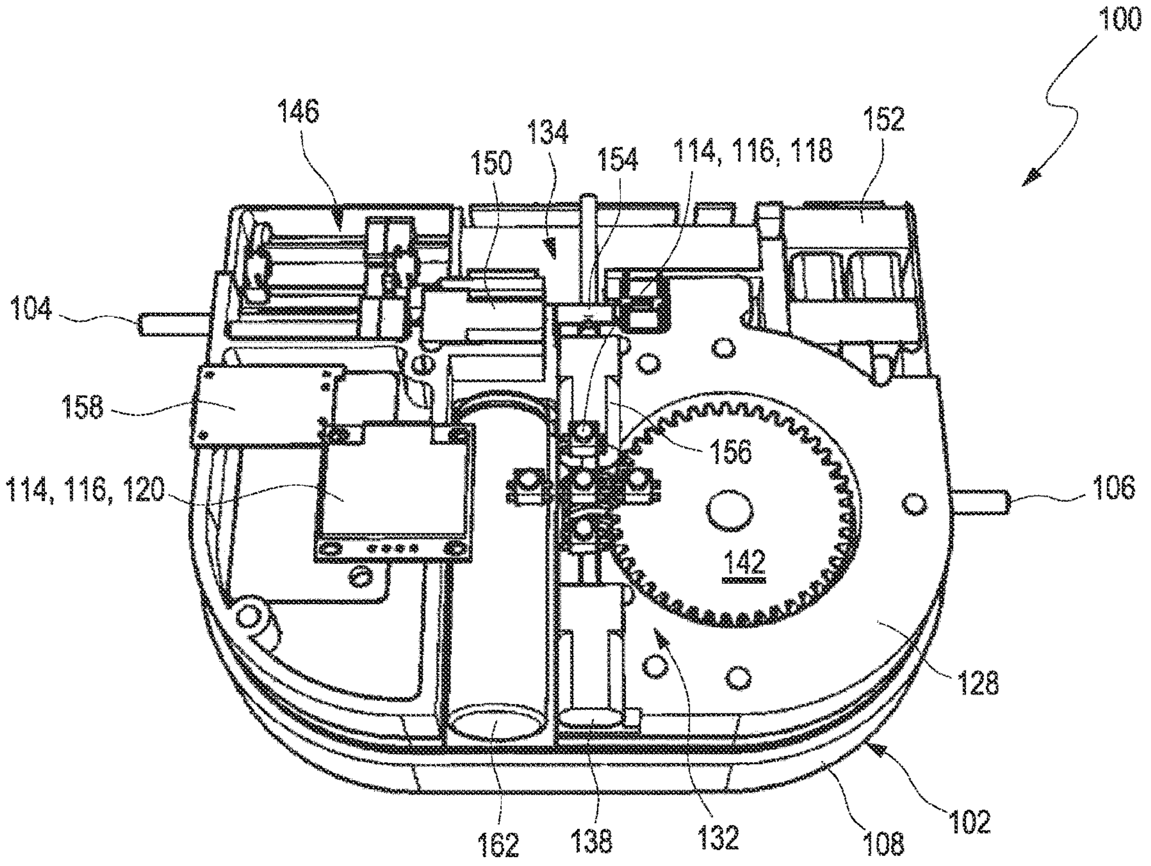
Figure 5:
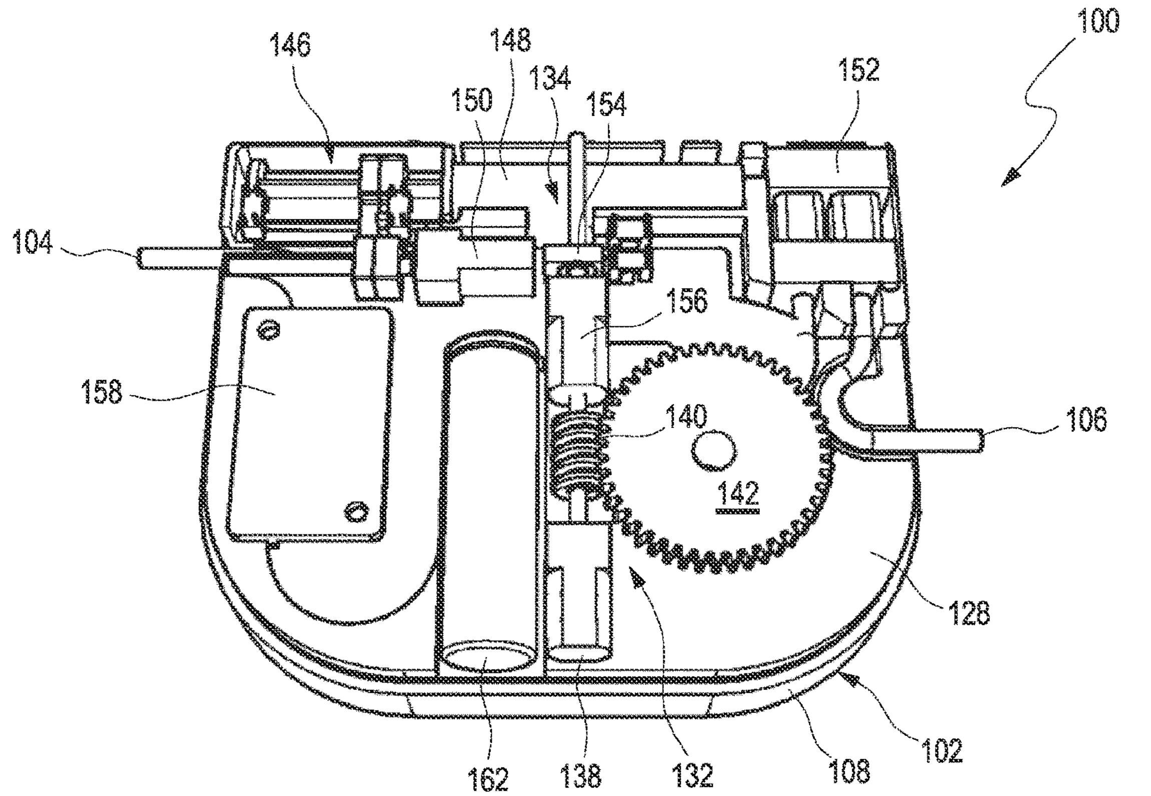
Figure 6:
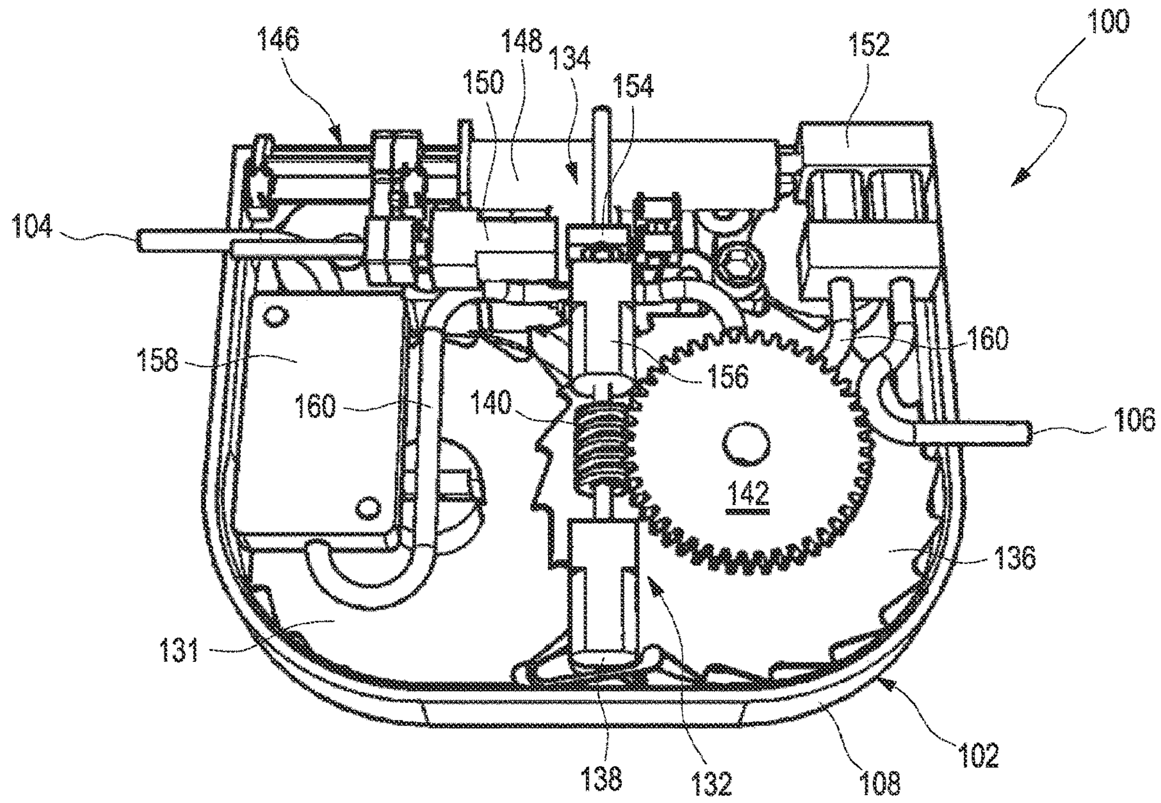
Figure 7:
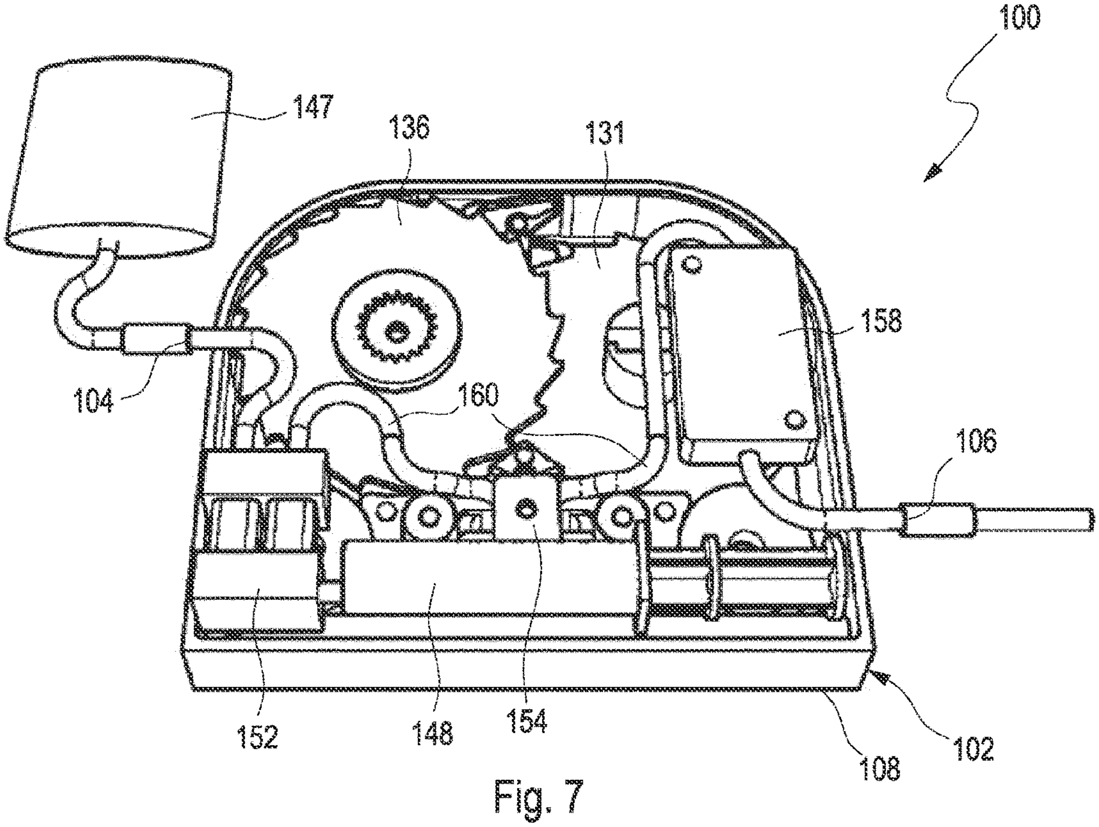
Figure 8:
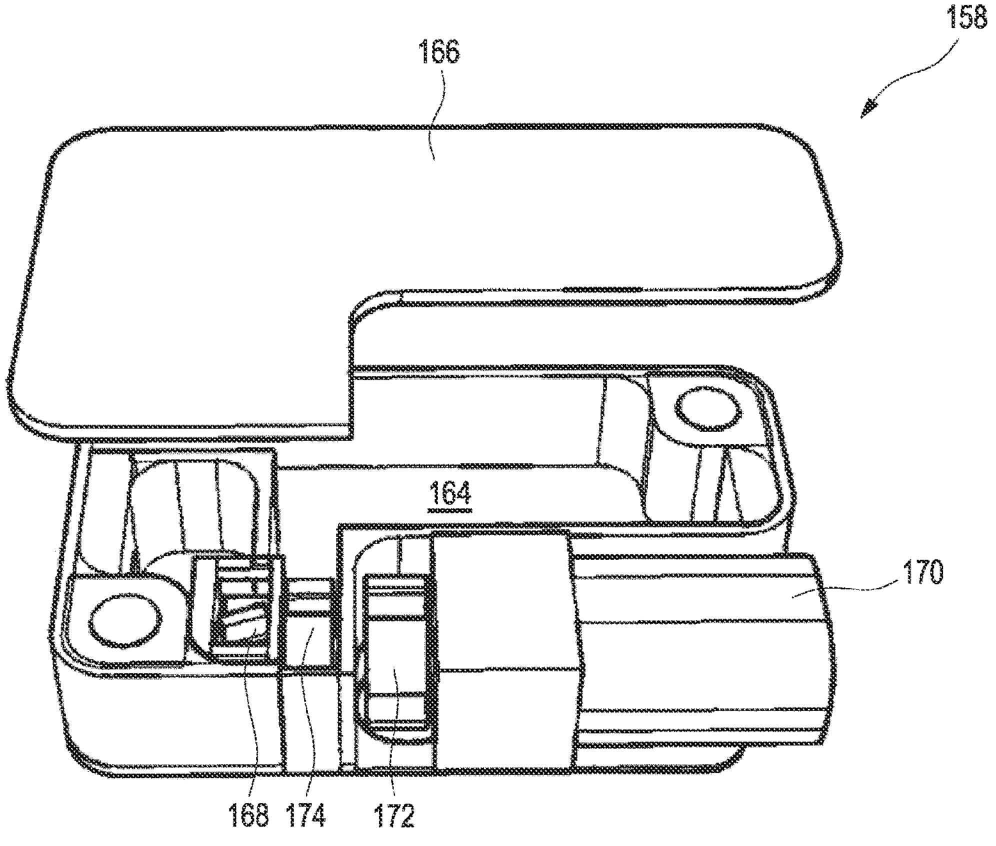
Figure 9:
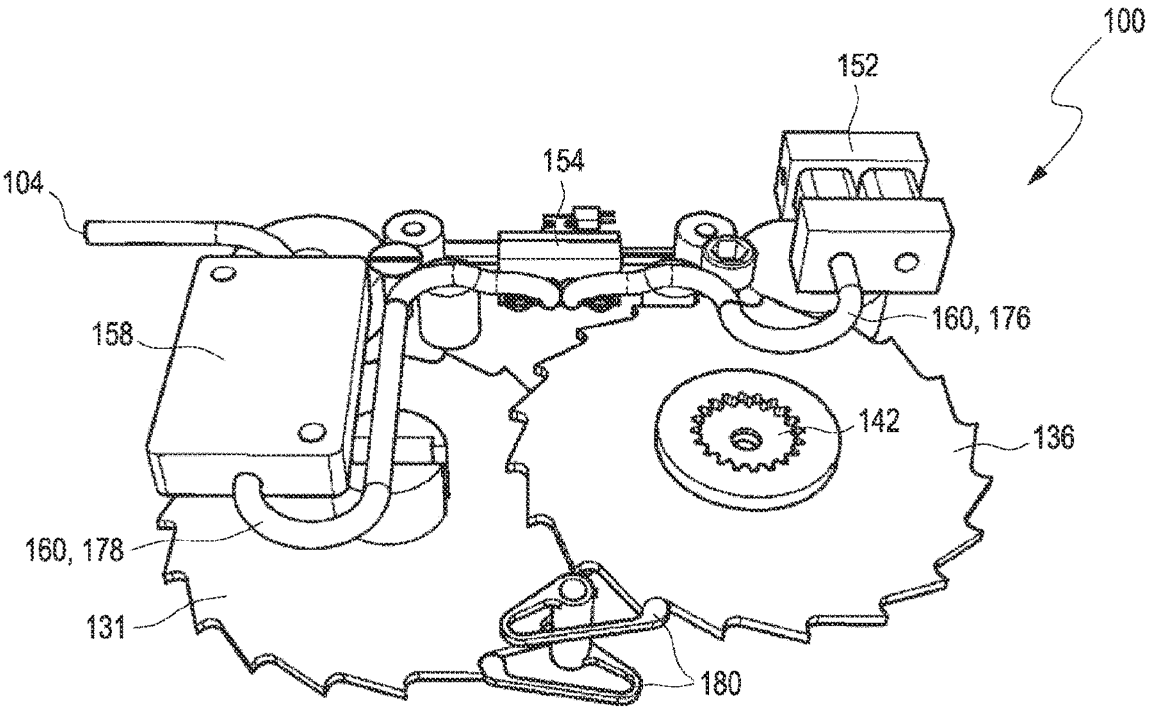
Figure 10:
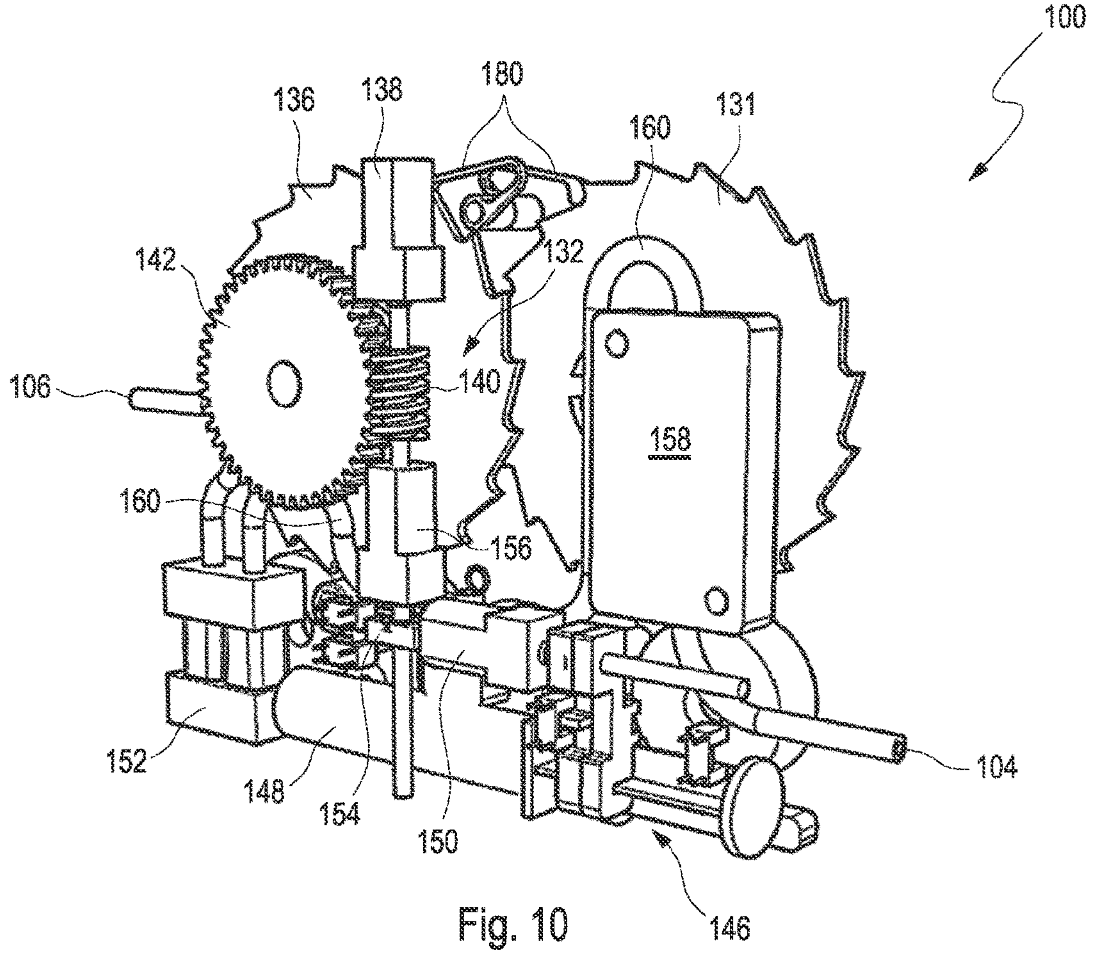
Figure 11:
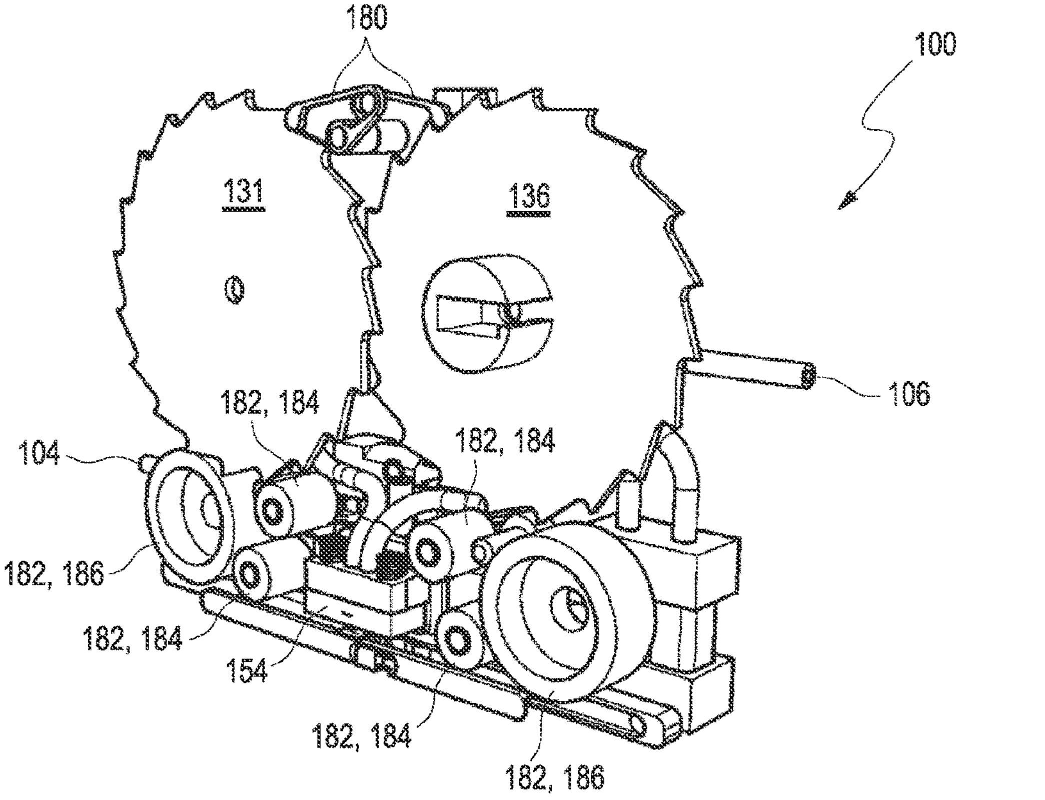
Figure 12:
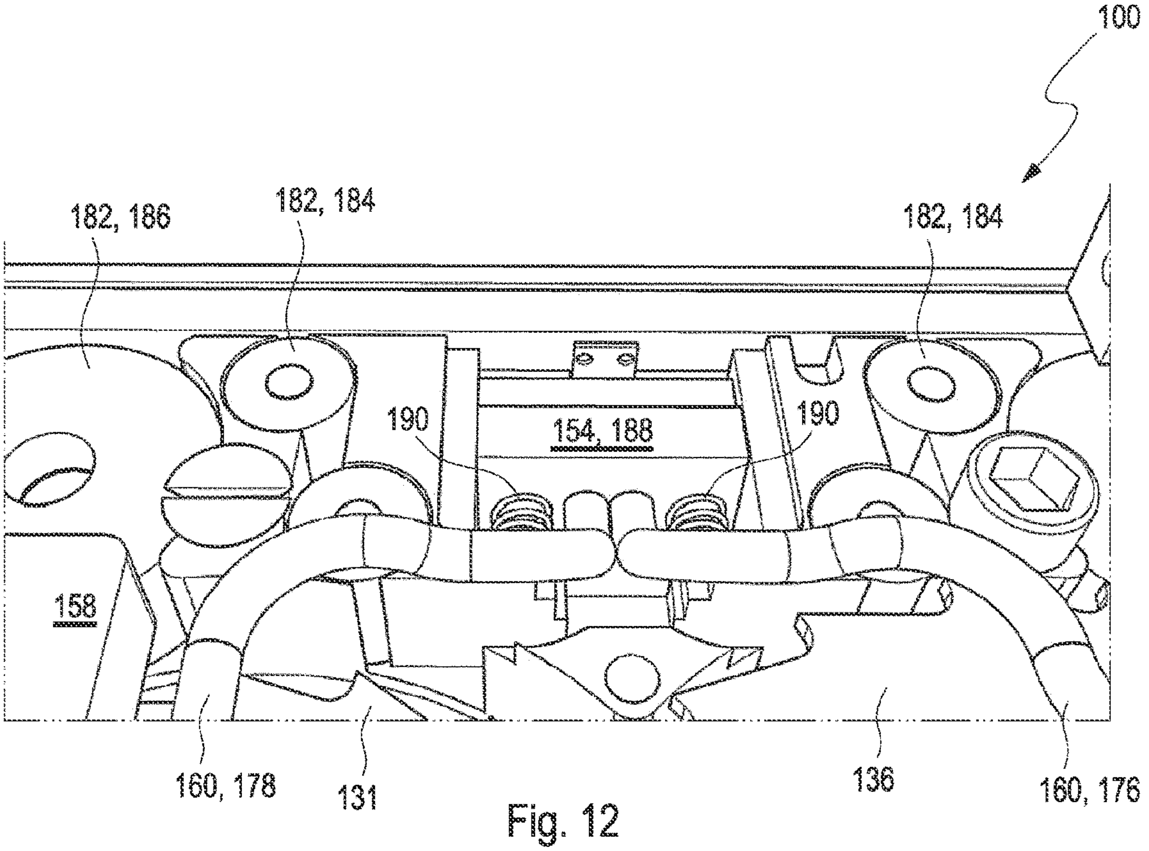
Figure 13:
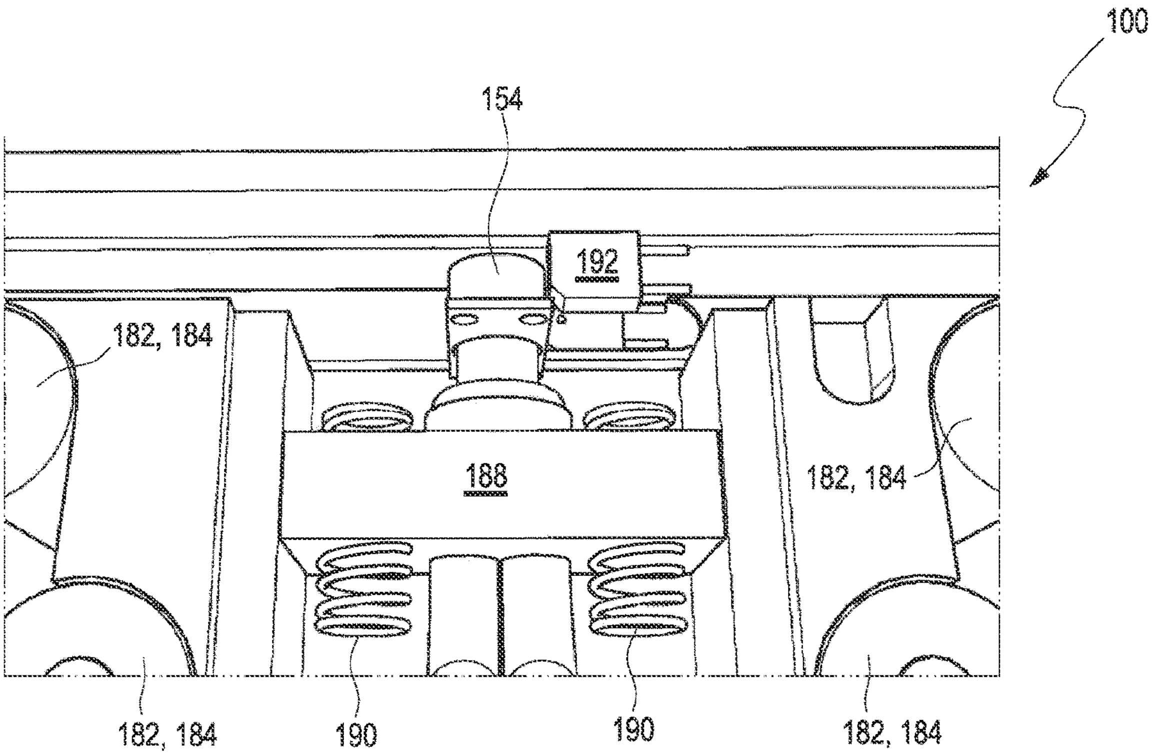
Figure 14:
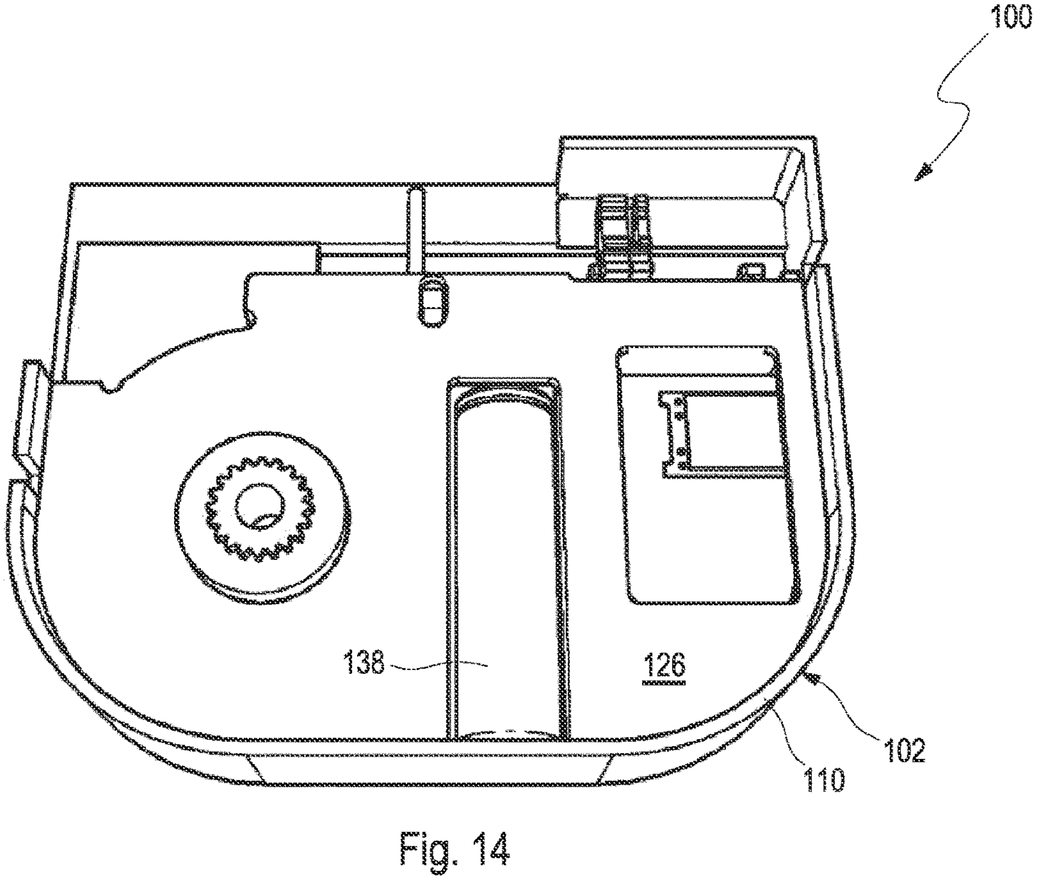
Figure 15:
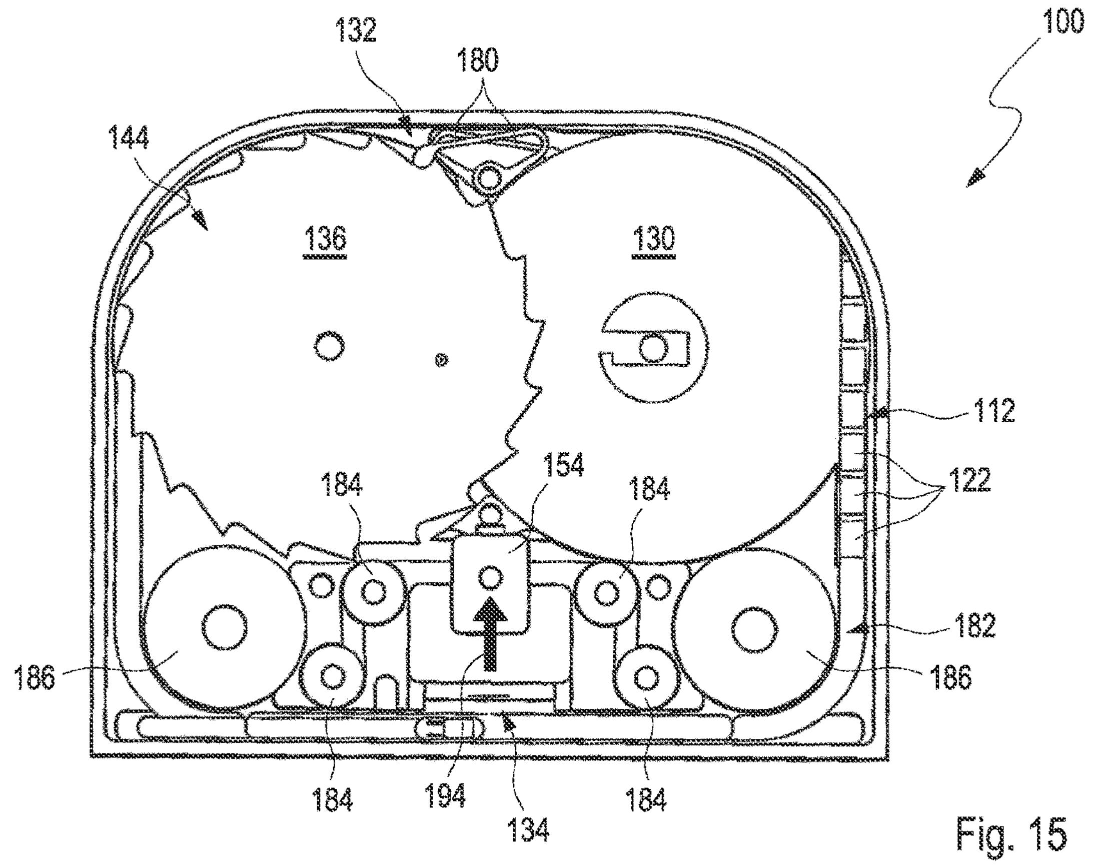

In the Figures:

FIG. 1 shows a perspective view of a delivery device according to an embodiment of the present invention, FIG. 2 shows a perspective view of a cartridge, FIG. 3 shows a perspective view of the delivery device with a cover removed, FIG. 4 shows a plan view of an interior of the delivery device, FIG. 5 shows a perspective view of an interior of the delivery device, FIG. 6 shows another perspective view of an interior of the delivery device, FIG. 7 shows another perspective view of an interior of the delivery device, FIG. 8 shows a perspective view of a mixing device, FIG. 9 shows another perspective view of an interior of the delivery device, FIG. 10 shows a front view of an interior of the delivery device, FIG. 11 shows a rear view of an interior of the delivery device, FIG. 12 shows another perspective view of an interior of the delivery device, FIG. 13 shows another perspective view of an interior of the delivery device, FIG. 14 shows a bottom view of the cover, and FIGS. 15 to 20 show perspective views of the delivery device in different operation states.

DETAILED DESCRIPTION OF THE EMBODIMENTS

FIG. 1 shows a perspective view of a delivery device 100 according to an embodiment of the present invention. The delivery device 100 is a portable delivery device. The delivery device 100 is configured to deliver a drug. The delivery device 100 comprises a housing 102. The housing 102 has an outlet 104, an inlet 106 and a cartridge compartment 108. The housing 102 may be formed by more than one part. For example, the housing 102 may comprise a cover 110. The cartridge compartment 108 is configured to receive a cartridge 112. The delivery device 100 further comprises a controller 114. The function of the controller 114 will be described in further detail below. The controller 114 comprises an interface (not shown in detail) configured to provide a communication link between the controller 114 and a remote electronic device (not shown in detail). The communication link is realized in a wireless or wired manner. The delivery device 100 further comprises an input device 116 configured to allow a user to input instructions to the controller 114. The input device 116 may comprise a keyboard or buttons 118. Alternatively or in addition, the input device 116 may comprise a display 120 configured to allow a user to input instructions to the controller 114. The delivery device 100 is reusable. Particularly, the cartridge compartment 108 is configured to allow a replacement of the cartridge 112.

FIG. 2 shows a perspective view of a cartridge 112. The cartridge 112 is filled with an active pharmaceutical formulation in solid form such as at least one antibiotic. Particularly, the cartridge 112 is filled with an active pharmaceutical formulation in powder form. In the present exemplary embodiment, the cartridge 112 comprises a plurality of compartments 122 each of which is filled with a predetermined amount of an active pharmaceutical formulation in powder form. As shown in FIG. 2, the cartridge 112 may be a blister tape 123. The compartments 122 are formed as closed pockets which are sealed by a foil 124. The foil 124 may be a thin protection foil. The cartridge 112 may optionally be provided with perforations 125.

FIG. 3 shows a perspective view of the delivery device 100 with the cover 110 removed. As shown in FIG. 3, interior components of the delivery device 100 may be protected by means of at least one cover plate 126. The cover plate 126 may be mounted to an inner housing portion 128 enclosing some constructional members of the delivery device 100 which will be explained in further detail below.

FIG. 4 shows a perspective view of an interior of the delivery device 100 with the cover plate 126 removed. FIG. 5 shows another perspective view of the delivery device 100 with the buttons 118 and the display 120 removed and the inner housing portion 128 partly removed. FIG. 6 shows another perspective view of the delivery device 100 with the inner housing portion 128 completely removed. FIG. 7 shows another perspective view of the delivery device 100 with the inner housing portion 128 completely removed. The cartridge compartment 108 is configured to receive a cartridge supply reel 130 (FIGS. 15 and 16) on which the cartridge 112 is reeled. The cartridge supply reel 130 may be disk-shaped. It has to be noted that FIGS. 4 to 7 show a cartridge gear 131 to which the cartridge supply reel 130 is connectable. The delivery device 100 comprises a transporting mechanism 132 configured to transport a predetermined amount of the active pharmaceutical formulation to a flushing position 134. In the present embodiment, the transporting mechanism is configured to transport the compartments 122 to the flushing position 134 in a subsequent order. The delivery device 100 further comprises a removal reel 136 configured to be reeled with the cartridge 112 after discharging of the active pharmaceutical formulation from at least one of the compartments 122 at the flushing position 134. The transporting mechanism 132 comprises a cartridge drive 138 configured to rotate the cartridge supply reel 130. Particularly, the cartridge drive 138 comprises a cartridge drive gear 140 configured to drive a removal reel gear 142 of the removal reel 136 to which the removal reel 136 is connectable. For example, the removal reel 136 may be formed as or connected to an empty compartment reservoir 144 (FIGS. 15 and 16) configured to receive empty or used compartments 122. The empty compartment reservoir 144 is replaceable. Thus, when the empty compartment reservoir 144 is full with used compartments 122 of the cartridge, it may be replaced by a new empty compartment reservoir 144. The empty compartment reservoir 144 is preferably designed such that any residual liquid from the discharged compartments 122 is restrained. The operation principle of the cartridge drive 138 is similar to a tape recorder. Particularly, the cartridge 112 is inserted into the cartridge compartment 108 and a leading end of the cartridge 112 and the blister tape 123, respectively, is fed towards the removal reel 136 while passing the flushing position 134. The feeding may be electrically or manually driven. Thereby, the cartridge 112 is also connected to the removal reel 136. When the cartridge drive 138 rotates the cartridge drive gear 140, the removal reel 136 is rotated due to the engagement of the cartridge drive gear 140 and the removal reel gear 142. Thereby, the cartridge 112 and the blister tape 123, respectively, is drawn while the cartridge supply reel 130 is rotated.

The delivery device 100 further comprises a pumping mechanism 146. The pumping mechanism 146 is connectable to a solvent reservoir 147 external to the housing 102 by means of the inlet 106. The pumping mechanism 146 is configured to deliver solvent from the solvent reservoir 147 towards the outlet 104. The pumping mechanism 146 comprises a pump 148 configured to suck a predetermined amount of the solvent from the solvent reservoir 147. For example, the pump 148 is a syringe pump. The pump 148 is driven by means of a pump drive 150 such as a linear drive. The pumping mechanism 146 further comprises a non-return valve 152 configured to block a flow of the sucked predetermined amount of the solvent back to the solvent reservoir 147.

The delivery device 100 further comprises a jetting piston 154 configured to enter the flushing position 134 and to flush the predetermined amount of the active pharmaceutical formulation from the flushing position 134 with a predetermined amount of the solvent towards the outlet 104. Particularly, the jetting piston 154 is configured to penetrate into one of the compartments 122 at the flushing position 134 and to discharge the active pharmaceutical formulation from the compartment 122 at the flushing position by means of flushing with the predetermined amount of the solvent. The jetting piston 154 is driven by means of a jetting piston drive 156 such as a linear drive. The jetting piston drive 156 is arranged adjacent the pump drive 150. It has to be noted that the jetting piston may comprise sealing members in order to avoid a leakage of the solvent when penetrating into the compartment. Further, the jetting piston 154 is designed such that the amount of solvent remaining in the flushed compartments 122 is minimized. Thus, the flushed compartments 122 supplied to the empty compartment reservoir 144 contain only negligible amounts of solvent. This effect may be further enhanced by spatial separation members and/or hydrophilic additives.

The delivery device 100 further comprises a mixing device 158 being in fluid communication with the output 104 and configured to mix the predetermined amount of the solvent and the predetermined amount of the active pharmaceutical formulation discharged from the compartment 122 at the flushing position 134 so as to provide or produce the drug. The delivery device 100 further comprises a fluid channel 160 connecting to the inlet 106 and the mixing device 158. The fluid channel 160 may be a tube. The jetting piston 154 is moveable between a retracted position, where the fluid channel 160 is blocked, and an extended position, where the jetting piston 154 provides a fluid communication with the fluid channel 160 and one of the compartments 122 at the flushing position 134.

The delivery device 100 further comprises a power source 162 configured to supply electrical power to at least one of the transporting mechanism 132, the pumping mechanism 146, the jetting piston 154 and the mixing device 158. In the embodiment shown, the power source 162 is configured to supply electrical power to the transporting mechanism 132, the pumping mechanism 146, the jetting piston 154 and the mixing device 158. The power source 162 may be a rechargeable power source.

FIG. 8 shows a perspective view of the mixing device 158. The mixing device 158 comprises a mixing chamber 164 configured to receive the predetermined amount of the solvent and the active pharmaceutical formulation discharged from the compartment 122 at the opening position 134. The mixing device 158 may further comprise a mixing chamber cover 166 configured to close the mixing chamber 164. The mixing device 158 further comprises a stirring member 168 located within the mixing chamber 164. The stirring member 168 is a magnetic stirring member. The mixing device 158 further comprises a stirring member drive 170 configured to rotate the stirring member 168. The stirring member drive 170 is spatially separated from the mixing chamber 164 such as by means of a wall portion defining the mixing chamber 164. In order to drive the stirring member 168, the stirring member drive 170 may comprise a rotor 172 with magnets and a contactless gear 174. The contactless gear 174 is connected to or integrally formed with the stirring member 168 and faces the rotor 172. The contactless gear 174 may be the magnetic part of the stirring member 168. Thus, when the rotor 172 rotates the contactless gear 174, the stirring member 168 integrally rotates therewith.

FIG. 9 shows another perspective view of the delivery device 100 with the housing 102 removed. As can be taken from FIG. 9, the fluid channel 160 may comprise a first connection portion 176 extending from non-return valve 152 to the jetting piston 154 and a second connection portion 178 extending from the jetting piston 154 to the mixing device 158. The second connection portion 178 is preferably rather short in order to avoid any residual solvent therein and in order to ensure that approximately all of the predetermined amount of the active pharmaceutical formulation is supplied to the mixing device 158. As can be further taken, the cartridge gear 131 and the removal reel gear 142 are each formed similar to a ratchet. Further, for each of the cartridge gear 131 and the removal reel gear 142, there is provided a pawl 180 pivotally arranged on a common axis. The pawls 180 engage the teeth of the ratchet-shaped cartridge gear 131 and the removal reel gear 142. Thus, a rotation of the cartridge gear 131 and the removal reel gear 142 is allowed only in one direction, which is a clockwise direction with respect to the illustration of FIG. 9, and is restricted in the opposite direction, which is a counter-clockwise direction with respect to the illustration of FIG. 9.

FIG. 10 shows a front view of an interior of the delivery device 100. From FIG. 11, the arrangement of the cartridge gear 131, the removal reel gear 142, the pumping mechanism 146, the jetting piston 154 and the mixing device 158 can be taken. Particularly, FIG. 10 shows the jetting piston 154, the jetting piston drive 156, the cartridge drive 136 and the cartridge drive gear 138 arranged at a central portion between the cartridge gear 131 and the removal reel gear 142. Further, with respect to the illustration of FIG. 10, the non-return valve 152 is located below the cartridge drive gear 140. Further, the pumping mechanism 146 is shown to be located at a lower end of the delivery device 100.

FIG. 11 shows a front view of an interior of the delivery device 100. The delivery device 100 further comprises a removing device 182 configured to remove the foil 124 sealing the compartments 122. The removing device 182 is at least partially arranged between the cartridge compartment 108 and the opening position 124. The removing device 182 comprises small tracking spools 184 and big tracking spools 186 for removing the foil 124. For example, removing device 182 comprises four small tracking spools 184 and two big tracking spools 186, wherein the small tracking spools 184 and the big tracking spools are arranged symmetrically next to the jetting piston 154. It is explicitly stated that the removing device 182 is optional and that alternatively, the jetting piston 154 may be configured to pierce the foil 124 sealing the compartments 122.

FIG. 12 shows another perspective view of an interior of the delivery device 100. FIG. 13 shows another perspective view of an interior of the delivery device 100. Particularly, FIGS. 12 and 13 show an enlarged detail of the delivery device 100 at an area around the jetting piston 154. FIG. 13 further shows the jetting piston 154 in the extended position. In order to move the jetting piston 154, the jetting piston drive 156 comprises a slider 188. Particularly, the slider 188 is driven by the jetting piston drive 156 which may be a linear drive located in the multiple use part of the device 100. The jetting piston drive 156 therefore moves the slider 188. The slider 188 comprises a liquid tight housing hold by springs, and the moveable jetting piston 154, which is tightly guided by liquid tight O-rings within the liquid tight housing. This allow an easy 2 step approach: firstly, a liquid tight contact to the cartridge 112 and the blister tape 123, respectively, and secondly, a liquid tight penetration into the compartment 122 and thereby removing all residual powder and liquid.

As can be further taken from FIGS. 12 and 13, at least one pressure spring 190 is arranged at the slider 188 allowing to provide for a 2-step water-proof contact jetting piston. The delivery device 100 further comprises at least one position sensor 192 configured to detect a position of the cartridge 112. The position sensor 192 may be arranged adjacent the jetting piston 154 so as to detect whether there is a compartment 122 at the flushing position 134.

FIG. 14 shows a bottom view of the cover 110. As can be taken from FIG. 14, the cover plate 126 may be connected to the cover 110. The cover plate 126 comprises orifices for accommodating the cartridge drive 138 and the mixing chamber 164. Optionally, the cartridge compartment 108 and the cartridge drive 138 may be at least partially located in the cover 110.

The controller 114 shown in FIGS. 1, 3 and 4 is at least configured to control operation of at least one of the transporting mechanism 132, the pumping mechanism 146, the jetting piston 154 and the mixing device 158. In the embodiment shown, the controller 114 is configured to control operation of the transporting mechanism 132, the pumping mechanism 146, the jetting piston 154 and the mixing device 158. The input device 116 allows a user to input instructions to the controller 114. Thus, the user may input instructions regarding the operation of the transporting mechanism 132, the pumping mechanism 146, the jetting piston 154 and the mixing device 158.

Optionally, the delivery device 100 may be modified as follows. The delivery device 100 may be a single use device. Thus, the cartridge 112 may be integrated into the housing 102. The delivery device 100 may further comprise a gas separator configured to separate gas, particularly air, from the solvent and the active pharmaceutical formulation discharged from the compartment 122 at the flushing position 134. The gas separator may be arranged adjacent the outlet 104 such as adjacent or within the mixing device 158. The delivery device 100 may further comprise a gas sensor configured to detect gas bubbles, such as air bubbles, within the solvent and the active pharmaceutical formulation discharged from the compartment 122 at the flushing position 134. The gas sensor may be further configured to detect a concentration of the active pharmaceutical formulation discharged from the compartment 122 at the flushing position 134 within the solvent. The delivery device 100 may further comprise a sterilizing device configured to sterilize the drug. The sterilizing device may be a UVC light source. The jetting piston 154 may be part of the cartridge 112. The mixing may be realized by micro-fluidic turbulences. The mixing device 158 may comprise an ultrasound source configured to emit ultrasound, wherein the ultrasound source is preferably arranged at a position allowing to emit ultrasound into the mixing chamber 164. The solvent reservoir 147 may be provided internal to the housing 102. The delivery device 100 may be configured to communicate with an in-situ blood sensor. The delivery device 100 may further comprise a filter upstream the outlet 104. The compartments 122 of the cartridge 112 may be pierced from two opposing sides. The active pharmaceutical formulation may be present as tablets or capsules. The cartridge may supply the active pharmaceutical formulation as a single member from which the respective amounts or doses are separated such as by means of a rotating knife. The pumping mechanism 132 may comprise another pump configured to discharged the solvent and the active pharmaceutical formulation from the mixing chamber 164. Thus, the solvent and the active pharmaceutical formulation may be temporarily stored within the mixing chamber 164 so as to increase the mixing time and the mixing quality.

Hereinafter, the operation of the delivery device 100 will be described in further detail with reference to FIGS. 15 to 20. FIGS. 15 to 20 show perspective views of the delivery device 100 in different operation states. At the beginning shown in FIG. 15, the cartridge supply reel 130 and the empty compartment reservoir 144 are inserted into the housing 102. The leading end of the cartridge 112 is transported to the removal reel 142 and the empty compartment reservoir 144. Further the jetting piston 154 is moved into the retracted position as indicated by arrow 194. Furthermore, in order to remove any air from the fluid channel 160 and the nonreturn valve 152, the fluid channel 160 is flushed with solvent from the solvent reservoir 147 which may take place before moving the jetting piston 154 into the retracted position.

Figure 16:
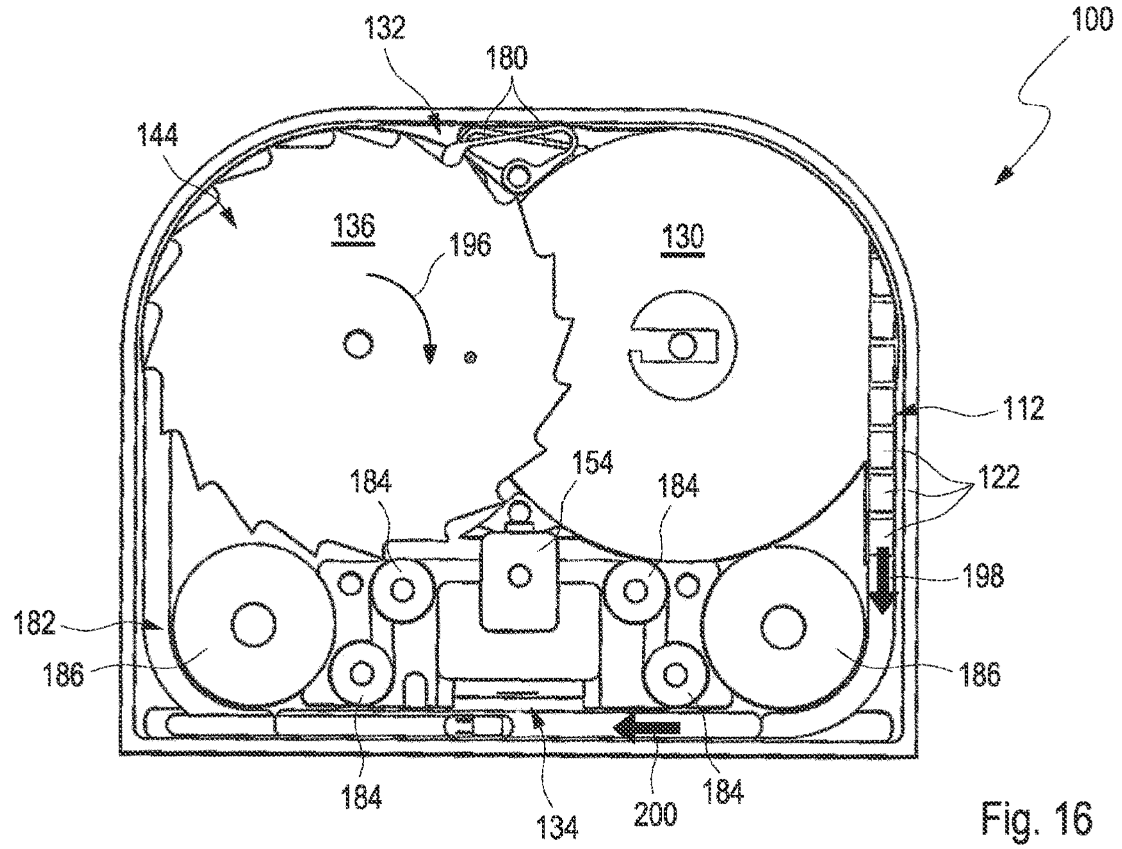

FIG. 16 shows a subsequent step, wherein the cartridge drive 138 and the cartridge drive gear 140 drive the removal reel gear 142 such that the removal reel gear 142 is rotated clockwise for one step defined by the teeth as indicated by arrow 196. At the same time, the cartridge gear 131 is rotated clockwise and the transporting mechanism 132 transports the first one of the compartments 122 in their row to the flushing position 134. The compartment 122 may be guided to the flushing position 134 on a curved path as indicated by arrows 198 and 200.

Figure 17:
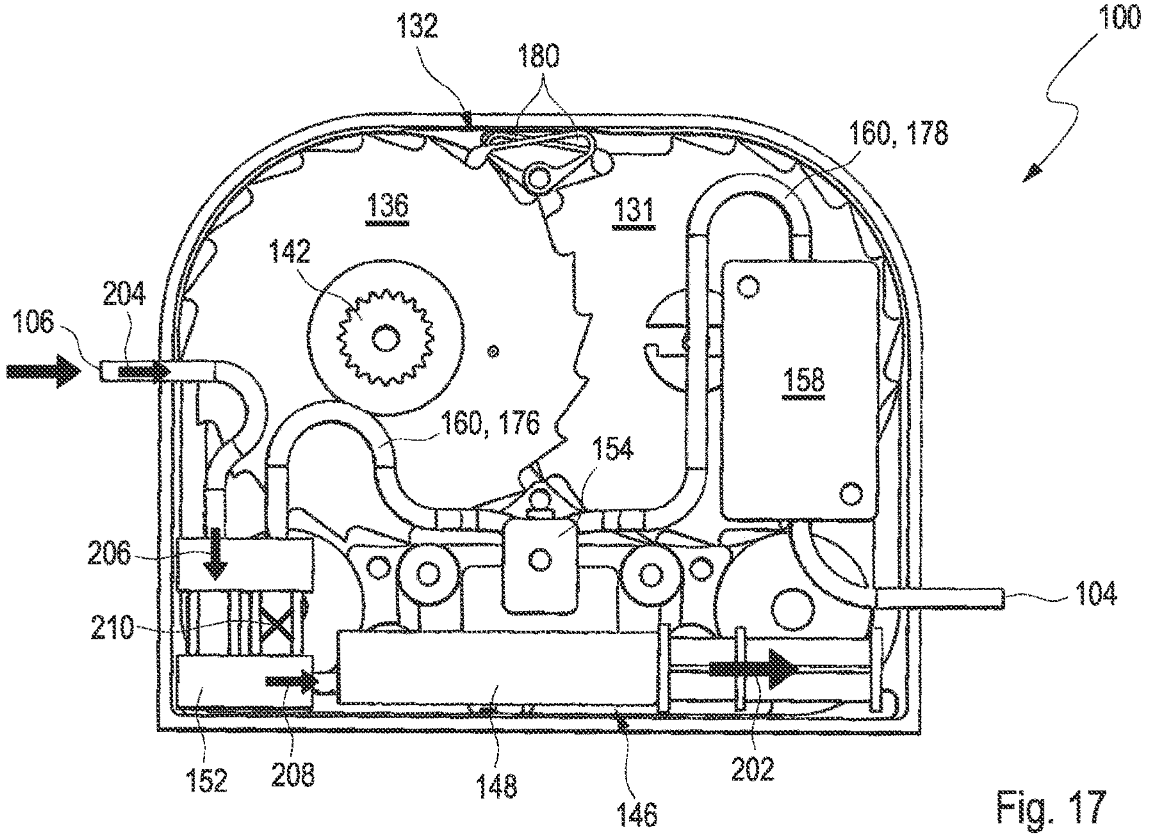

Subsequently, as shown in FIG. 17, the pumping mechanism 146 sucks a predetermined amount of solvent from the solvent reservoir 147 at the inlet 106. For this purpose, the pumping mechanism 146 moves a piston of the syringe pump 148 in a direction away from the nonreturn valve 152 as indicated by arrow 202. The solvent may be a solution comprising NaCl. The solvent flows from the inlet 106 through the non-return valve 152 into the syringe pump 148 as indicated by arrows 204, 206 and 208. The non-return valve 152 restricts the solvent from flowing further towards the jetting piston 154 within the first connection portion 176 extending from non-return valve 152 to the jetting piston 154 as indicated by cross 210.

Figure 18:
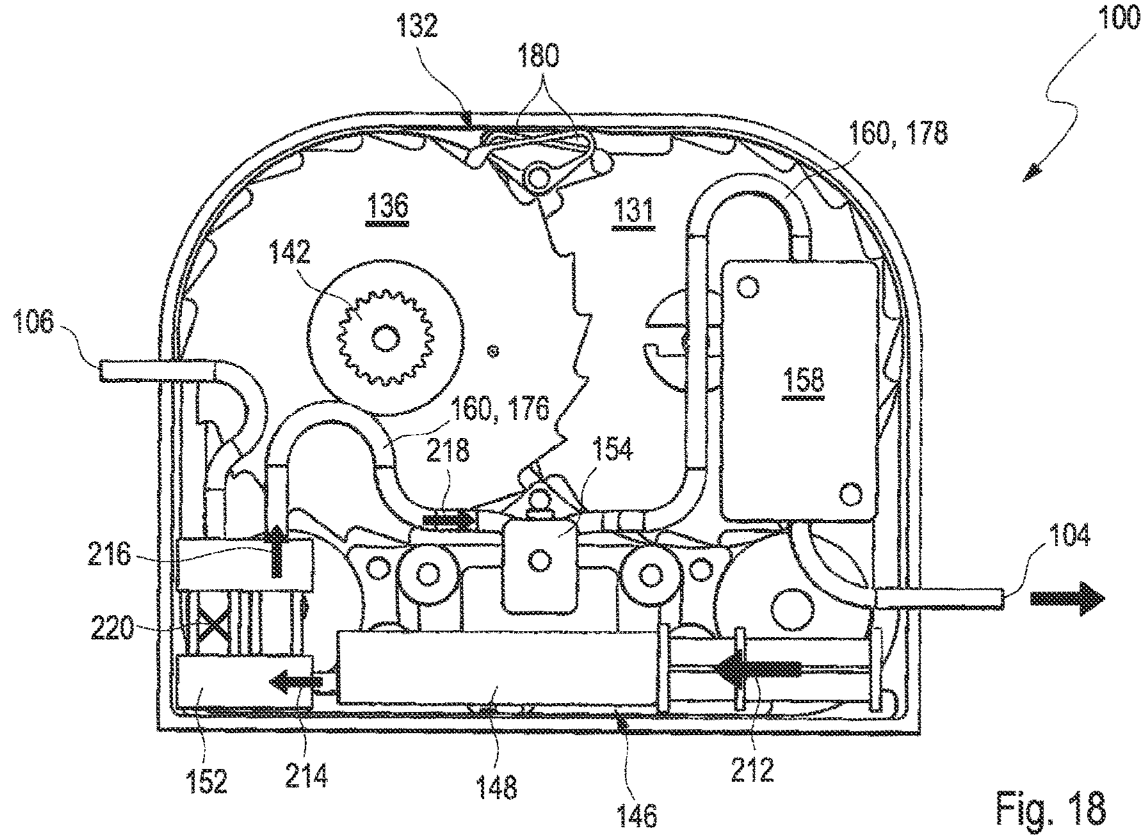

Subsequently, as shown in FIG. 18, the pumping mechanism 146 pumps the predetermined amount of solvent towards the jetting piston 154. For this purpose, the pumping mechanism 146 moves the piston of the syringe pump 148 in a direction towards the non-return valve 152 as indicated by arrow 212. The solvent flows out of the pump 148 through the non-return valve 152 into the first connection portion 176 extending from non-return valve 152 to the jetting piston 154 as indicated by arrows 214, 216 and 218. The non-return valve 152 restricts the solvent from flowing back to the inlet 106 and the solvent reservoir as indicated by cross 220.

Figure 19:
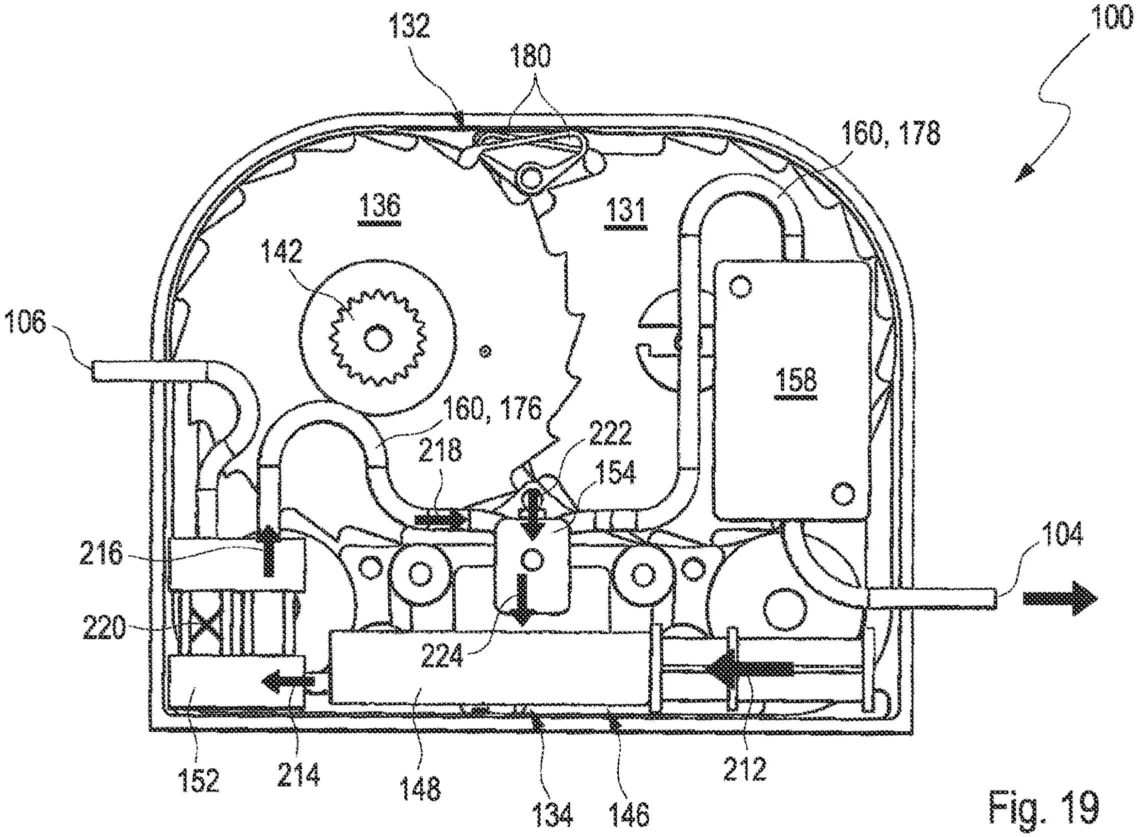

Further and at the same time, as shown in FIG. 19, the jetting piston 154 moves into the extended position as indicated by arrow 222. Thereby, the jetting piston 154 enters the flushing position 134 and penetrates into the compartment 122. The jetting piston 154 then flushes the compartment 122 at the flushing position 134 with the predetermined amount of the solvent so as to discharge the predetermined amount of the active pharmaceutical formulation from the compartment 122 at the flushing position 134 as indicated by arrow 224.

Figure 20:
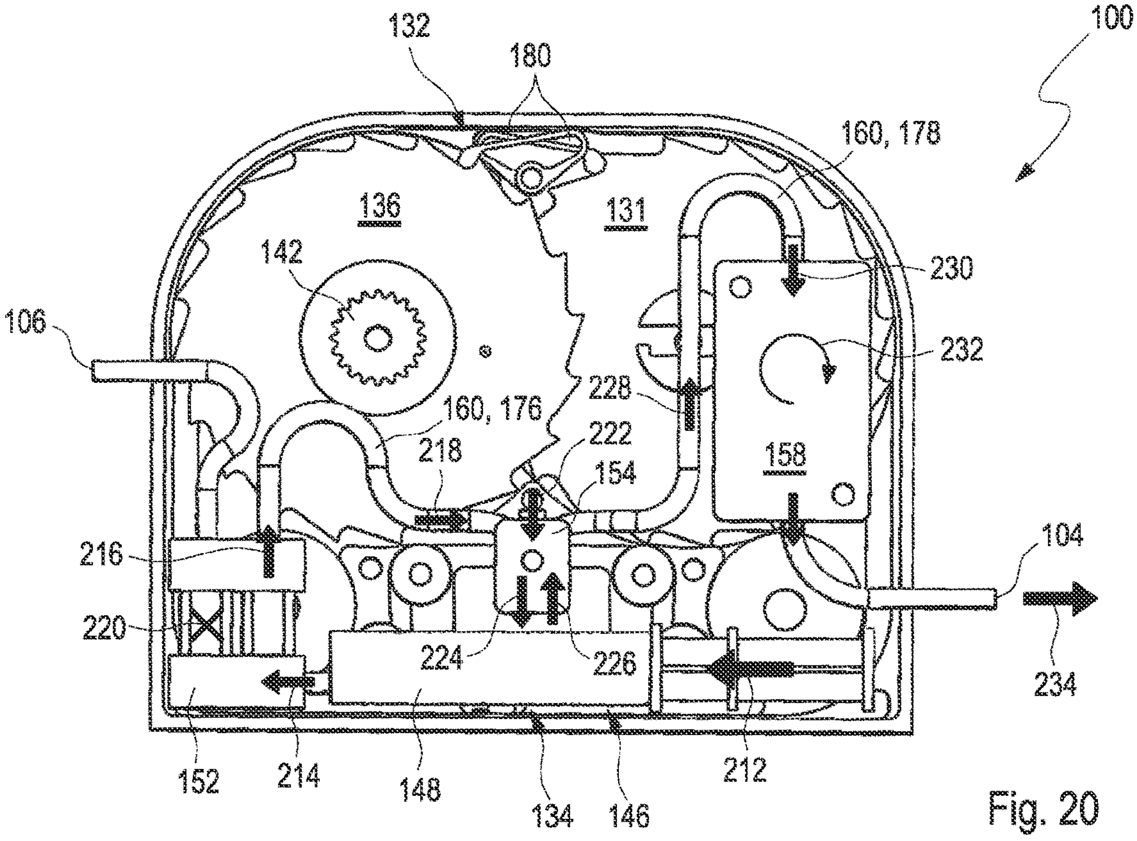

Finally, as shown in FIG. 20, the predetermined amount of the active pharmaceutical formulation flushed from the compartment 122 at the flushing position 134 and the predetermined amount of the solvent enter the second connection portion 178 of the fluid channel 160 extending from the jetting piston 154 to the mixing device 158 and flow into the mixing device 158 and the mixing chamber 164, respectively, as indicated by arrows 226, 228 and 230. In the mixing device 158 and the mixing chamber 164, respectively, the active predetermined amount of the pharmaceutical formulation flushed from the compartment 122 at the flushing position 134 and the predetermined amount of the solvent are mixed by means of driving the stirring member 168 as indicated by arrow 232. Thus, the drug is provided. The drug then is discharged from the mixing device 158 and the delivery device 100 at the outlet 104 as indicated by arrow 234. Thus, the provided drug is ready for infusion or administration to a patient.

The operation described with reference to FIGS. 15 to 20 may be repeated as appropriate. In this case, the used compartment 122 is transported from the flushing position 134 to the removal reel 142 and the empty compartment reservoir 144. Further, the next compartment 122 in the row of the cartridge 112 is transported to the flushing position 134. After all of the active pharmaceutical formulation of the cartridge 112 has been used and all compartments have been discharged, the cartridge supply reel 130 and the empty compartment reservoir 144 may be replaced.

The invention claimed is:

1. A delivery device for delivering a drug, comprising:

a housing having an outlet, and a cartridge compartment configured to receive a cartridge filled with an active pharmaceutical formulation in powder form;

a transporting mechanism configured to transport a predetermined amount of the active pharmaceutical formulation to a flushing position;

a pumping mechanism connectable to a solvent reservoir and configured to deliver solvent from the solvent reservoir towards the outlet;

a jetting piston configured to enter the flushing position and to produce a jet of the solvent so as to flush the predetermined amount of the active pharmaceutical formulation from the flushing position with a predetermined amount of the solvent towards the outlet;

a fluid channel in fluid communication with the solvent reservoir and the outlet, wherein the jetting piston is moveable between a retracted position, where the fluid channel is blocked, and an extended position, where the jetting piston provides a fluid communication with the fluid channel and the flushing position; and a controller at least configured to control operation of at least one of the transporting mechanism, the pumping mechanism, the jetting piston.

2. The delivery device according to claim 1, wherein the cartridge comprises a plurality of compartments each of which is filled with the predetermined amount of the active pharmaceutical formulation, wherein the transporting mechanism is configured to transport the compartments to the flushing position in a subsequent order.

3. The delivery device according to claim 1, wherein the cartridge compartment is configured to receive a cartridge supply reel on which the cartridge is reeled.

4. The delivery device according to claim 1, wherein the transporting mechanism comprises a cartridge drive configured to rotate the cartridge supply reel.

5. The delivery device according to claim 1, further comprising a removal reel configured to be reeled with the cartridge after discharging of the active pharmaceutical formulation from at least one of the compartments at the flushing position, wherein the cartridge drive comprises a cartridge drive gear configured to mesh with a removal reel gear of the removal reel, wherein the cartridge supply reel is concertedly rotatable with the removal reel.

6. The delivery device according to claim 1, further comprising a removing device configured to remove a foil sealing the compartments arranged at least partially between the cartridge compartment and the flushing position or the jetting piston is configured to pierce a foil sealing the compartments.

7. The delivery device according to claim 1, wherein the cartridge is a blister tape, wherein the compartments are formed as closed pockets sealed by a foil.

8. The delivery device according to claim 1, wherein the pumping mechanism comprises a syringe pump, configured to suck the predetermined amount of the solvent from the solvent reservoir and a non-return valve configured to block a flow of the sucked predetermined amount of the solvent back to the solvent reservoir.

9. The delivery device according to claim 1, further comprising a mixing device being in fluid communication with the outlet and configured to mix the predetermined amount of the solvent and predetermined amount of the active pharmaceutical formulation flushed from the flushing position so as to provide the drug, wherein the mixing device comprises a mixing chamber configured to receive the predetermined amount of the solvent and the predetermined amount of the active pharmaceutical formulation flushed from the flushing position.

10. The delivery device according to claim 1, further comprising a rechargeable power source configured to supply electrical power to at least one of the transporting mechanism, the pumping mechanism, the jetting piston, the controller and the mixing device.

11. The delivery device according to claim 1, further comprising an input device configured to allow a user to input instructions to the controller.

12. The delivery device according to claim 1, further comprising a gas sensor configured to detect air bubbles within the predetermined amount of the solvent and the predetermined amount of the active pharmaceutical formulation flushed from the flushing position, the gas sensor is further configured to detect a concentration of the predetermined amount of the active pharmaceutical formulation solved within the predetermined amount of the solvent.

13. The delivery device according to claim 1, wherein the delivery device is configured to communicate with an in-situ blood sensor.

14. The delivery device according to claim 1, wherein the delivery device is a single use device or wherein the delivery device is reusable, wherein the cartridge compartment is configured to allow a replacement of the cartridge.

* * * * *